United States Patent
Votaw et al.

(10) Patent No.: US 8,021,130 B2
(45) Date of Patent: Sep. 20, 2011

(54) APPARATUS AND METHOD FOR HANDLING FLUIDS AT NANO-SCALE RATES

(75) Inventors: Gregory A. Votaw, Durham, NC (US); Charles A. Buckner, Chapel Hill, NC (US); Daniel M. Hartmann, East Lansing, MI (US); William Karsh, Belmont, MA (US); Frank Anthony Montefusco, Durham, NC (US); Joshua T. Nevill, El Cerrito, CA (US); Mehul Patel, Ambler, PA (US); David W. Wyrick, Durham, NC (US); Hugh C. Crenshaw, Durham, NC (US)

(73) Assignee: AB Sciex, LLC, Framingham, MA (US)

( * ) Notice: Subject to any disclaimer, the term of this patent is extended or adjusted under 35 U.S.C. 154(b) by 1067 days.

(21) Appl. No.: 11/719,518

(22) PCT Filed: Aug. 10, 2006

(86) PCT No.: PCT/US2006/031166
§ 371 (c)(1),
(2), (4) Date: May 16, 2007

(87) PCT Pub. No.: WO2007/021817
PCT Pub. Date: Feb. 22, 2007

(65) Prior Publication Data
US 2009/0142198 A1 Jun. 4, 2009

Related U.S. Application Data

(60) Provisional application No. 60/707,421, filed on Aug. 11, 2005.

(51) Int. Cl.
*F04B 17/00* (2006.01)

(52) U.S. Cl. .......................... 417/415; 604/152; 417/32
(58) Field of Classification Search .................. 417/415, 417/417, 32; 604/152, 155
See application file for complete search history.

(56) References Cited

U.S. PATENT DOCUMENTS 3,554,673 A * 1/1971 Schwartz ...................... 417/412
(Continued)

OTHER PUBLICATIONS

PCT Written Opinion of the International Search Authority, PCT/US06/31166, mailed Dec. 31, 2007.

(Continued)

*Primary Examiner* — Devon C. Kramer
*Assistant Examiner* — Peter J Bertheaud
(74) *Attorney, Agent, or Firm* — Sheldon Mak & Anderson

(57) ABSTRACT

Apparatus and Method for Handling Fluids at Nano-Scale Rates. A linear displacement pump produces non-pulsatile liquid flow rates as low as the nl/mm range. The pump includes a servo motor, a gear reduction, a lead screw, a linear stage, a barrel, and a plunger extending into the barrel and coupled to the stage. A microfluidic interconnect device can be coupled to the barrel. One or more of these pumps can be disposed in a thermally controlled pump assembly that includes a pump housing, a thermally conductive body disposed in the housing and including first and second opposing sides, and a temperature regulating element such as a thermoelectric device disposed in thermal contact with the thermally conductive body on a side thereof opposite to the barrel or barrels of the pumps.

11 Claims, 24 Drawing Sheets

U.S. PATENT DOCUMENTS

| | | | | |
|---|---|---|---|---|
| 4,089,624 | A | * | 5/1978 | Nichols et al. ............... 417/362 |
| 4,406,158 | A | * | 9/1983 | Allington .................... 73/61.57 |
| 4,435,173 | A | * | 3/1984 | Siposs et al. ................. 604/155 |
| 4,451,364 | A | | 5/1984 | Higgins et al. |
| 4,509,904 | A | * | 4/1985 | MacAskill et al. .......... 417/568 |
| 4,934,907 | A | | 6/1990 | Kroner |
| 5,037,396 | A | | 8/1991 | Streeter |
| 5,573,515 | A | | 11/1996 | Wilson et al. |
| 6,354,637 | B1 | | 3/2002 | Coronado |
| 2004/0164013 | A1 | * | 8/2004 | Takao et al. ................ 210/198.2 |
| 2005/0061722 | A1 | * | 3/2005 | Takao et al. .................. 210/137 |

OTHER PUBLICATIONS

International Search Report, PCT/US06/31166, mailed Dec. 31, 2007.

Bousse, L. et al., "Electrokinetically Controlled Microfluidic Analysis Systems," Annu. Rev. Biophys. Biomol. Struct., 2000, vol. 29. pp. 155-181.

Chien, R.L. et al., "Multiport flow-control system for lab-on-a-chip microfluidic devices," Fresenius J. Anal. Chem., 2001, vol. 371, pp. 106-111.

Kerby, M. et al., "A fluorogenic assay using pressure-driven flow on a microchip," Electrophoresis, 2001, vol. 22, pp. 3916-3923.

\* cited by examiner

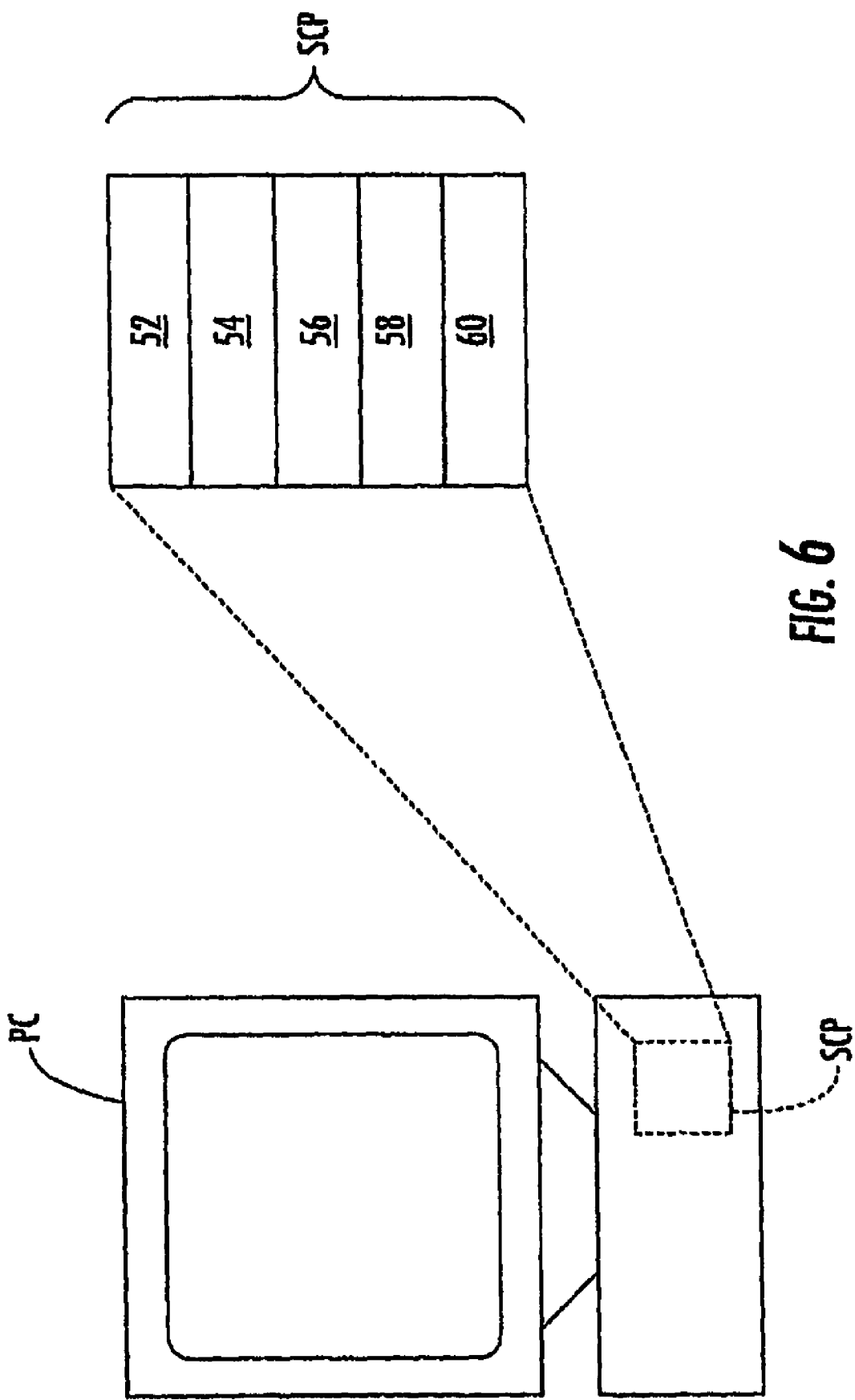

APPARATUS AND METHOD FOR HANDLING FLUIDS AT NANO-SCALE RATES

CROSS-REFERENCE TO RELATED APPLICATIONS

This application is the U.S. national stage of International Application No. PCT/US06/31166, filed Aug. 10, 2006 and entitled APPARATUS AND METHOD FOR HANDLING FLUIDS AT NANO-SCALE RATES, which claims the benefit of U.S. Patent Application Ser. No. 60/707,421, filed Aug. 11, 2005, the disclosure of which is incorporated herein by reference in its entirety. The disclosures of the following U.S. Provisional Applications, commonly owned and simultaneously filed Aug. 11, 2005, are all incorporated by reference in their entirety: U.S. Provisional Application entitled APPARATUS AND METHOD FOR HANDLING FLUIDS AT NANO-SCALE RATES, U.S. Provisional Application No. 60/707,421; U.S. Provisional Application entitled MICROFLUIDIC BASED APPARATUS AND METHOD FOR THERMAL REGULATION AND NOISE REDUCTION, U.S. Provisional Application No. 60/707,330; U.S. Provisional Application entitled MICROFLUIDIC METHODS AND APPARATUSES FOR FLUID MIXING AND VALVING, U.S. Provisional Application No. 60/707,329; U.S. Provisional Application entitled METHODS AND APPARATUSES FOR GENERATING A SEAL BETWEEN A CONDUIT AND A RESERVOIR WELL, U.S. Provisional Application No. 60/707,286; U.S. Provisional Application entitled MICROFLUIDIC SYSTEMS, DEVICES AND METHODS FOR REDUCING DIFFUSION AND COMPLIANCE EFFECTS AT A FLUID MIXING REGION, U.S. Provisional Application No. 60/707,220; U.S. Provisional Application entitled MICROFLUIDIC SYSTEMS, DEVICES AND METHODS FOR REDUCING NOISE GENERATED BY MECHANICAL INSTABILITIES, U.S. Provisional Application No. 60/707,245; U.S. Provisional Application entitled MICROFLUIDIC SYSTEMS, DEVICES AND METHODS FOR REDUCING BACKGROUND AUTOFLUORESCENCE AND THE EFFECTS THEREOF, U.S. Provisional Application No. 60/707,386; U.S. Provisional Application entitled MICROFLUIDIC CHIP APPARATUSES, SYSTEMS, AND METHODS HAVING FLUIDIC AND FIBER OPTIC INTERCONNECTIONS, U.S. Provisional Application No. 60/707,246; U.S. Provisional Application entitled METHODS FOR CHARACTERIZING BIOLOGICAL MOLECULE MODULATORS, U.S. Provisional Application No. 60/707,328; U.S. Provisional Application entitled METHODS FOR MEASURING BIOCHEMICAL REACTIONS, U.S. Provisional Application No. 60/707,370; U.S. Provisional Application entitled METHODS AND APPARATUSES FOR REDUCING EFFECTS OF MOLECULE ADSORPTION WITHIN MICROFLUIDIC CHANNELS, U.S. Provisional Application No. 60/707,366; U.S. Provisional Application entitled PLASTIC SURFACES AND APPARATUSES FOR REDUCED ADSORPTION OF SOLUTES AND METHODS OF PREPARING THE SAME, U.S. Provisional Application No. 60/707,288; U.S. Provisional Application entitled BIOCHEMICAL ASSAY METHODS, U.S. Provisional Application No. 60/707,374; U.S. Provisional Application entitled FLOW REACTOR METHOD AND APPARATUS, U.S. Provisional Application No. 60/707,233; and U.S. Provisional Application entitled MICROFLUIDIC SYSTEM AND METHODS, U.S. Provisional Application No. 60/707,384.

TECHNICAL FIELD

The present disclosure generally relates to microfluidic processing of reagents and analysis of reaction products. More specifically, the present disclosure relates to apparatuses and methods for moving fluids at continuously variable, nano-scale flow rates in a smooth, non-pulsatile manner, and under precise thermal control if desired.

BACKGROUND ART

Biochemical and biological assays are a primary tool utilized in many aspects of drug discovery, including fundamental research in biochemistry and biology to describe novel phenomena, analysis of large numbers of compounds, screening of compounds, clinical tests applied during clinical trials, and ultimately diagnostic tests during administration of drugs. Many biological and biochemical assays require measurement of the response of a biological or biochemical system to different concentrations of one reagent, such as an inhibitor, a substrate, or an enzyme. Typically, discrete steps of biochemical concentration are mixed within a proscribed range. The number of concentrations measured is limited by the number of dilution steps, which are limited in practice by the time and effort required to make the discrete dilutions, by the time and effort to process the resulting individual reactions, by reagent consumption as the number of reactions increases, and more strictly by pipetting errors that limit the resolution of discrete steps.

As technology advances in drug development, miniaturization and automation are active areas of innovation, with primary drivers being decreased cost (through decreased reagent use and decreased manpower) and improved data quality (through finer process control and increased process reliability). Improvements in data quality and automation frequently convey additional advantages that permit new scientific approaches to questions. Automation, if sufficiently extensive, can include software that permits automatic work scheduling to improve efficiency or statistical process control for process improvement. Again, these improvements achieve greater reliability, use less manpower, and improve throughput.

Microfluidic systems, including labs-on-a-chip (LoCs) and micro-total analysis systems (μ-TAS), are currently being explored as an alternative to conventional approaches that use microtiter plates. The miniaturization afforded by microfluidic systems has the potential to greatly reduce the amount of reagent needed to conduct high-throughput screening. Thus far, commercial microfluidic systems have shown some promise in performing point measurements, but have not been employed to mix concentration gradients and particularly continuous gradients due to technologic limitations. In particular, several challenges remain in the design of industry-acceptable microfluidic systems. Apart from cost and manufacture related issues, many sources of such challenges relate to the fact that, in a micro-scale or sub-micro-scale environment, certain fluid characteristics such as viscosity, surface tension, shear resistance, thermal conductivity, electrical conductivity, molecular diffusivity, and the like, take on a much more dominant role than other, more easily manageable factors such as weight and gravity. In addition, controlling the signal-to-noise ratio becomes much more challenging when working with nano-scale volumes and flow rates, as certain sources of noise that typically are inconsequential in macroscopic applications now become more noticeable and thus deleterious to the accuracy of data acquisition instruments.

One important consideration in the design of a microfluidic system is the means utilized for driving liquid flows. Pressure-based, electrokinetics-based, and displacement-based pumping techniques have been explored. As a general matter, pressure pumping generates a proscribed pressure difference at the two ends of a pipe. Examples of the use of pressure-driven flow in a microfluidic format, in which step-wise concentration gradients were generated in the course of enzymology-related experiments, are disclosed in Chien et al., "Multiport flow-control system for lab-on-a-chip microfluidic devices", *Fresenius J Anal Chem* 371, 106-11 (2001) and Kerby et al., "A fluorogenic assay using pressure-driven flow on a microchip", *Electrophoresis* 22, 3916-23 (2001).

Electrokinetic pumping techniques generally include electro-osmotic, electrophoretic, electro-wetting, and electrohydrodynamic (EHD) pumping, each of which operates on different principles than pressure and displacement pumping. For a general treatment of some types of electrokinetic pumping, see Bousse, et al., "Electrokinetically controlled microfluidic analysis systems", *Annu Rev Biophys Biomol Struct* 29, 155-81 (2000).

Displacement pumping generates a proscribed flow rate directly, typically by pushing a piston or other boundary against a volume of liquid. The change in volume generated by motion of the solid boundary, therefore, is the flow rate generated by the pump. A typical example of a displacement pump is a syringe pump.

The term "displacement micropumps" has been used to describe two categories of pumps. The first category includes pumps that are themselves microscopic, and are basically miniaturized versions of macroscopic centrifugal pumps, gear pumps, peristaltic pumps, rotary pumps, and the like. Some of these pumps can be fabricated on-chip using MEMS or other microfabrication techniques, and are capable of low flow rates. However, such pumps suffer from a number of limitations: they generate pulsatile flows, and the flow rates from these pumps depend in a non-linear way upon a number of factors, including the age of the pumps, the frequency with which the pumps are "pulsed", and their precise location on a chip. These factors make it difficult to use such pumps to achieve reliable and reproducible flow rates of the sort necessary to achieve controlled gradients. Additionally, these pumps are fabricated with semiconductor and MEMS manufacturing techniques. This fabrication can be extremely costly and time-consuming, and results in a specific pump-architecture that is not flexible or reconfigurable and, frequently, is not manufacturable according to industry-acceptable considerations.

The second category of displacement micropumps includes macroscopic pumps that are capable of delivering microscopic flow rates. Again, there are a wide variety of such pumps available. Some micropumps have minimum flow rates of tens of microliters per minute. Unfortunately, a μl/min-scale flow rate is three orders of magnitude larger than the nl/min-scale flow rates often desired by researchers interested in microfluidics-based assays and experiments, and nl/min flow rates have heretofore been unattainable with these pumps. The pumps that are of primary interest in this category are so-called syringe pumps. A syringe pump typically consists of a motor connected to, for example, a worm gear that pushes the plunger of a syringe, causing liquid to flow out of the syringe tip. The syringe is often coupled to whatever device or instrument requires the flow. Syringe pumps designed for low flow rates are commercially available. Some of these pumps are capable of delivering μl/min-scale flow rates. Most of these pumps, however, use stepper motors, which become unacceptably pulsatile as the step rate is decreased to drive very slow flows. While some syringe pumps use servomotors, they are not capable of practicing stable, precise, controllable flow rates below the μl/min scale. For many applications, such as dispensing predefined aliquots of liquid, pulsatile flows are acceptable. However, when a linear, or smoothly varying, continuous gradient is desired, the quality of flow from pumps utilizing stepper motors decreases as the flow rate drops, adding noise to the gradient at the extremes of the gradient. In contrast, a servomotor is capable of moving at any speed (in non-discrete steps), because the rotation rate is directly controlled (not the frequency of steps).

Another factor in the design of microfluidic systems is the microfluidic interconnect, which generally provides a fluidic interface between a microfluidic component and either another microfluidic component or a macrofluidic component. As with all fluidic connections, a microfluidic interconnect should create a mechanically stable, fluid-tight connection between the components that can contain the pressures of the fluids. Additionally, a microfluidic interconnect should have a small dead volume so as not to approach or exceed the volume of the microfluidic device associated therewith. Moreover, dead volumes should be kept small for the sake of efficiency because, by nature, a sample is neither prepared nor analyzed in a dead volume. In addition, a microfluidic interconnect should not have outpockets, create rapid expansions of channel volumes, or introduce sharp turns, so that the interconnect does not generate excessive dispersion of chemical concentration gradients. The interconnect should not trap bubbles because this affects the accuracy of displacement flow rates, and, as a result, affects time of flight and concentration. Finally, the interconnect should be manufacturable in a precise, reliable, and repeatable manner.

One consideration when employing a microfluidic system to acquire data is thermal noise. For example, room temperature fluctuations can influence flow rates and measurements of the flows and of chemical reactions. There are several reasons that temperature fluctuations cause noise. Among other things, the fluorescent dyes often utilized to monitor reaction rates are pH dependent, and many pH buffers are temperature dependent. The rates of reaction of enzymes are strongly temperature dependent. Also, physical changes to components in the system due to thermal expansion can affect flows and measurements. Thermal changes in the fluid paths can change flow characteristics, flow rates and fluid velocities. For example, a change of only 0.01% volume over 1 minute for a volume of 10 microliters equals a volume change of 1 nl, which is problematic if flows of 1 nl/min are being studied. When trying to control flow rates of nl/min, very small changes in volume can produce significant changes in the observed flows. Thermal changes in the alignment of components, similarly, can have undesired effects owing to the small sizes of microfluidic components. For example, consider a photodetector that has been positioned to perform optical measurements in the center of a microfluidic channel that is 10 μm wide. Thermal expansion of only a few micrometers can move the photodetector off-center or even entirely away from the channel. Similarly, many microfluidic chips are made of bonded or laminated materials. These laminated structures are highly prone to flexing due to thermal expansion of the laminates, especially if one laminate expands more than another. This flexing of the chip can change the position of a microchannel that has been, for example, positioned into the beam of a laser for photo-measurement of a chemical reaction in the channel.

The embodiments described herein are provided to address these and other problems attending current microfluidic systems.

SUMMARY

According to one embodiment, a linear displacement pump is provided for producing low, non-pulsatile liquid flow rates. The pump comprises a servo motor drive, a lead screw, a stage, a barrel, and a plunger. The servo motor drive has a gear reduction suitable for producing liquid flow rates grading from between about 0 nl/min and 500 nl/min, with a precision as low as approximately 0.1 nl/min. The lead screw is coupled to the motor drive for rotatable actuation thereby, and has a thread pitch suitable for producing liquid flow rates grading from between about 0 nl/min and 500 nl/min, with a precision as low as approximately 0.1 nl/min. The stage engages the lead screw and is linearly translatable thereby. The barrel is adapted for containing a liquid, and has an internal volume ranging from approximately 5 to approximately 500 μl. The plunger extends into the barrel and is coupled to the stage for translation therewith.

According to another embodiment, a linear displacement pump for producing low, non-pulsatile liquid flow rates comprises a servo motor drive, a lead screw coupled to the motor drive for rotatable actuation thereby, a stage engaging the lead screw and linearly translatable thereby, a barrel for containing a liquid, a plunger, and a coupling device. The plunger comprises an elongate portion extending into the barrel and a head portion of larger cross-sectional area than the elongate portion. The coupling device is adapted for removably coupling the plunger to the stage. The coupling device comprises a plunger mount attached to the stage, and a tightening plate adjustably secured to the stage. The head portion of the plunger is securable between the plunger mount and the tightening plate.

According to yet another embodiment, a pump assembly comprises a pump housing, a thermally conductive body disposed in the housing, a pump mounted to the housing, and a temperature regulating element mounted to the housing. The thermally conductive body comprises first and second opposing sides. The pump comprises a barrel for containing liquid. The barrel is disposed in an interior of the housing in thermal contact with the first side of the body. A temperature regulating element is in thermal contact with the second side of the body.

According to still another embodiment, a microfluidic interconnect apparatus comprises a first annular member, a gasket, a second annular member, a female fitting, and a third annular member. The first annular member has a first bore for coaxially receiving a syringe barrel. The gasket extends into the first bore and has an upstream gasket end, a downstream gasket end, and a gasket bore axially extending between the ends for fluidly communicating with the barrel. The second annular member is coaxially disposed about the first annular member and the gasket, and it is removably attached to the first annular member. The female fitting abuts the downstream gasket end and has a female fitting bore fluidly communicating with the gasket bore. The third annular member is coaxially disposed about the second annular member, and is axially adjustable relative thereto for biasing the female fitting against the gasket. A fluidly sealed, generally axial flow path is defined from the gasket bore to the female fitting bore.

In a method for flowing a liquid according to a low flow rate, non-pulsatile, laminar regime, a liquid is pushed out from a barrel at a non-pulsatile flow rate between about 0 nl/min and 500 nl/min, with a precision as low as 0.1 nl/min by contacting the liquid with a boundary. The boundary is axially driven through the barrel by a displacement pump comprising a continuously variable-speed servo motor.

According to a method for actively regulating the temperature of a liquid contained in a pump, at least an approximate temperature of a liquid contained in a barrel is measured. The barrel is coupled to a linear displacement pump, and is disposed in a pump housing that is in thermal contact with a barrel support member. The liquid temperature or an approximate value thereof is measured by measuring a temperature of the barrel support member. The temperature of the liquid is actively regulated at a desired set point temperature by operating a temperature regulating element. The temperature regulating element is mounted on a side of the barrel support member opposite to the barrel. The temperature regulating element establishes a thermal gradient through the barrel support member toward or alternately away from the barrel based on the measured temperature to substantially maintain the liquid at the set point temperature.

According to a method for regulating temperature in a pump assembly, at least an approximate temperature is measured for a plurality of respective pump components of a plurality of linear displacement pumps disposed in a pump housing. In one aspect, the plurality of pump components comprise a plurality of respective barrels containing respective liquids. In other aspects, the plurality of pump components can include other features or elements, such as pump stages, plungers, coupling devices, and/or fluidic interconnects. The method further comprises minimizing out-of-phase thermal pumping in the pumps by regulating the temperature of corresponding pump components as between each pump. The thermal pumping can be minimized by minimizing temperature differences among the respective pumps and minimizing differences in temperature rate changes among the respective pumps.

According to another embodiment, a pump assembly is disclosed. The pump assembly can include a housing comprising first and second compartments. The first and second compartments can be thermally isolated. Further, the pump assembly can include a pump positioned in the first compartment. The pump assembly can also include a switching valve positioned in the first compartment and in fluid communication with the pump. In addition, the pump assembly can include a reagent cartridge positioned in the second compartment and being in fluid communication with the switching valve for receiving fluid from the pump. The reagent cartridge can be thermally isolated from the pump and switching valve.

According to yet another embodiment, a method for inserting fluid into a microfluidic chip is disclosed. The method can include a step for providing a housing comprising first and second compartments, the first and second compartments being thermally isolated. In addition, the method can include a step for providing a pump positioned in the first compartment. The method can also include a step for providing a switching valve positioned in the first compartment and in fluid communication with the pump. Further, the method can include a step for providing a reagent cartridge positioned in the second compartment and being in fluid communication with the switching valve for receiving fluid from the pump. The reagent cartridge can be thermally isolated from the pump and switching valve. In addition, the reagent cartridge can be in communication with a microfluidic chip. The method can also include a step for positioning reagent in the reagent cartridge. Further, the method can include a step for positioning hydraulic fluid in the pump. The method can also include a step for operating the pump to displace the hydraulic fluid such that the hydraulic fluid moves the reagent into the microfluidic chip.

According to another embodiment, a microfluidic interconnect apparatus is disclosed. The apparatus can include a first annular member having an upstream end and a downstream end and having a first bore extending between the ends for coaxially receiving a syringe barrel. Further, the apparatus can include a female fitting abutting the downstream end of the first annular member and a second bore fluidly communicating with the first bore. The apparatus can also include a second annular member coaxially disposed about the first annular member, and axially movable with respect to the first annular member for biasing the female fitting against a face end of the syringe barrel.

Therefore, it is an object to provide an apparatus and method for handling fluids at nano-scale rates.

An object having been stated hereinabove, and which is addressed in whole or in part by the present disclosure, other objects will become evident as the description proceeds when taken in connection with the accompanying drawings as best described hereinbelow.

BRIEF DESCRIPTION OF THE DRAWINGS

FIG. 6 is a schematic view of system control software provided in accordance with embodiments disclosed herein;

DETAILED DESCRIPTION

Figure 1:
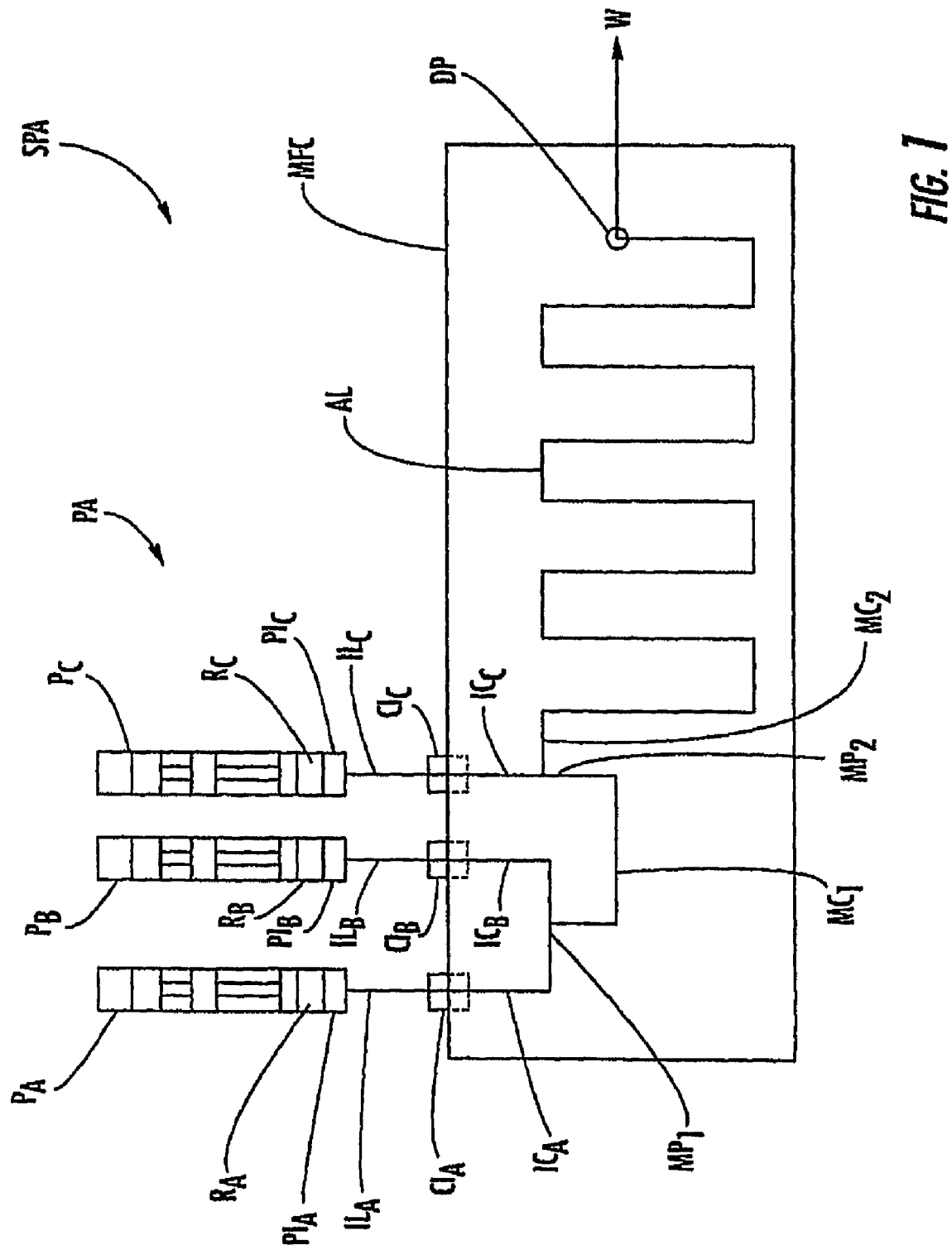
FIG. 1 is a schematic view of a sample processing apparatus including a pump assembly and a microfluidic chip provided in accordance with embodiments disclosed herein.

Microfluidic chips, systems, and related methods are described herein which incorporate improvements for reducing or eliminating noise in the fluid mix concentration. These microfluidic chips, systems, and methods are described with regard to the accompanying drawings. It should be appreciated that the drawings do not constitute limitations on the scope of the disclosed microfluidic chips, systems, and methods.

As used herein, the term "microfluidic chip," "microfluidic system," or "microfluidic device" generally refers to a chip, system, or device which can incorporate a plurality of interconnected channels or chambers, through which materials, and particularly fluid borne materials can be transported to effect one or more preparative or analytical manipulations on those materials. A microfluidic chip is typically a device comprising structural or functional features dimensioned on the order of mm-scale or less, and which is capable of manipulating a fluid at a flow rate on the order of μl/min or less. Typically, such channels or chambers include at least one cross-sectional dimension that is in a range of from about 1 μm to about 500 μm. The use of dimensions on this order allows the incorporation of a greater number of channels or chambers in a smaller area, and utilizes smaller volumes of reagents, samples, and other fluids for performing the preparative or analytical manipulation of the sample that is desired.

Microfluidic systems are capable of broad application and can generally be used in the performance of biological and biochemical analysis and detection methods. The systems described herein can be employed in research, diagnosis, environmental assessment and the like. In particular, these systems, with their micron scales, nanoliter volumetric fluid control systems, and integratability, can generally be designed to perform a variety of fluidic operations where these traits are desirable or even required. In addition, these systems can be used in performing a large number of specific assays that are routinely performed at a much larger scale and at a much greater cost.

A microfluidic device or chip can exist alone or may be a part of a microfluidic system which, for example and without limitation, can include: pumps for introducing fluids, e.g., samples, reagents, buffers and the like, into the system and/or through the system; detection equipment or systems; data storage systems; and control systems for controlling fluid transport and/or direction within the device, monitoring and controlling environmental conditions to which fluids in the device are subjected, e.g., temperature, current and the like.

As used herein, the term "channel" or "microfluidic channel" can mean a cavity formed in a material by any suitable material removing technique, or can mean a cavity in combination with any suitable fluid-conducting structure mounted in the cavity such as a tube, capillary, or the like.

As used herein, the term "reagent" generally means any flowable composition or chemistry. The result of two reagents merging or combining together is not limited to any particular response, whether a biological response or biochemical reaction, a dilution, or otherwise.

In referring to the use of a microfluidic chip for handling the containment or movement of fluid, the terms "in", "on", "into", "onto", "through", and "across" the chip generally have equivalent meanings.

As used herein, the term "communicate" (e.g., a first component "communicates with" or "is in communication with" a second component) and grammatical variations thereof are used herein to indicate a structural, functional, mechanical, electrical, optical, or fluidic relationship, or any combination thereof, between two or more components or elements. As such, the fact that one component is said to communicate with a second component is not intended to exclude the possibility that additional components may be present between, and/or operatively associated or engaged with, the first and second components.

As used herein, the terms "measurement", "sensing", and "detection" and grammatical variations thereof have interchangeable meanings; for the purpose of the present disclosure, no particular distinction among these terms is intended.

Embodiments disclosed herein comprise hardware and/or software components for controlling liquid flows in microfluidic devices and measuring the progress of miniaturized biochemical reactions occurring in such microfluidic devices. As the description proceeds, it will become evident that the various embodiments disclosed herein can be combined according to various configurations to create a technologic system or platform for implementing micro-scale or sub-micro-scale analytical functions. One or more of these embodiments can contribute to or attain one or more advantages over prior art technology, including: (1) 1000-fold reduction in the amount of reagent needed for a given assay or experiment; (2) elimination of the need for disposable assay plates; (3) fast, serial processing of independent reactions; (4) data readout in real-time; (5) improved data quality; (6) more fully integrated software and hardware, permitting more extensive automation of instrument function, 24/7 operation, automatic quality control and repeat of failed experiments or bad gradients, automatic configuration of new experimental conditions, and automatic testing of multiple hypotheses; (7) fewer moving parts and consequently greater robustness and reliability; and (8) simpler human-instrument interface. As the description proceeds, other advantages may be recognized by persons skilled in the art.

Referring now to FIG. 1, a sample processing apparatus, generally designated SPA, is illustrated according to certain embodiments. Generally, sample processing apparatus SPA can be utilized for precisely generating and mixing continuous concentration gradients of reagents in the nl/min to µl/min range, particularly for initiating a biological response or biochemical reaction from which results can be read after a set period of time. Sample processing apparatus SPA generally comprises a reagent introduction device advantageously provided in the form of a pump assembly, generally designated PA, and a microfluidic chip MFC. Pump assembly PA comprises one or more linear displacement pumps such as syringe pumps or the like. For mixing two or more reagents, pump assembly PA comprises at least two or more pumps. In the illustrated embodiment in which three reagents can be processed (e.g., reagent $R_A$, $R_B$, and $R_C$), sample processing apparatus SPA includes a first pump $P_A$, a second pump $P_B$, and a third pump $P_C$. Sample processing apparatus SPA is configured such that pumps $P_A$, $P_B$ and $P_C$ are disposed off-chip but inject their respective reagents $R_A$, $R_B$ and $R_C$ directly into microfluidic chip MFC via separate input lines $IL_A$, $IL_B$ and $IL_C$ such as fused silica capillaries, polyetheretherketone (such as PEEK® available from Upchurch Scientific of Oak Harbor, Wash.) tubing, or the like. In some embodiments, the outside diameter of input lines $IL_A$, $IL_B$ and $IL_C$ can range from approximately 50-650 µm. In some embodiments, each pump $P_A$, $P_B$ and $P_C$ interfaces with its corresponding input line $IL_A$, $IL_B$ and $IL_C$ through a pump interconnect $PI_A$, $PI_B$ and $PI_C$ designed for minimizing dead volume and bubble formation, and with replaceable parts that are prone to degradation or wear. Pump interconnects $PI_A$, $PI_B$ and $PI_C$ according to some embodiments are described in more detail hereinbelow with reference to FIGS. 11A and 11B.

Figure 2:
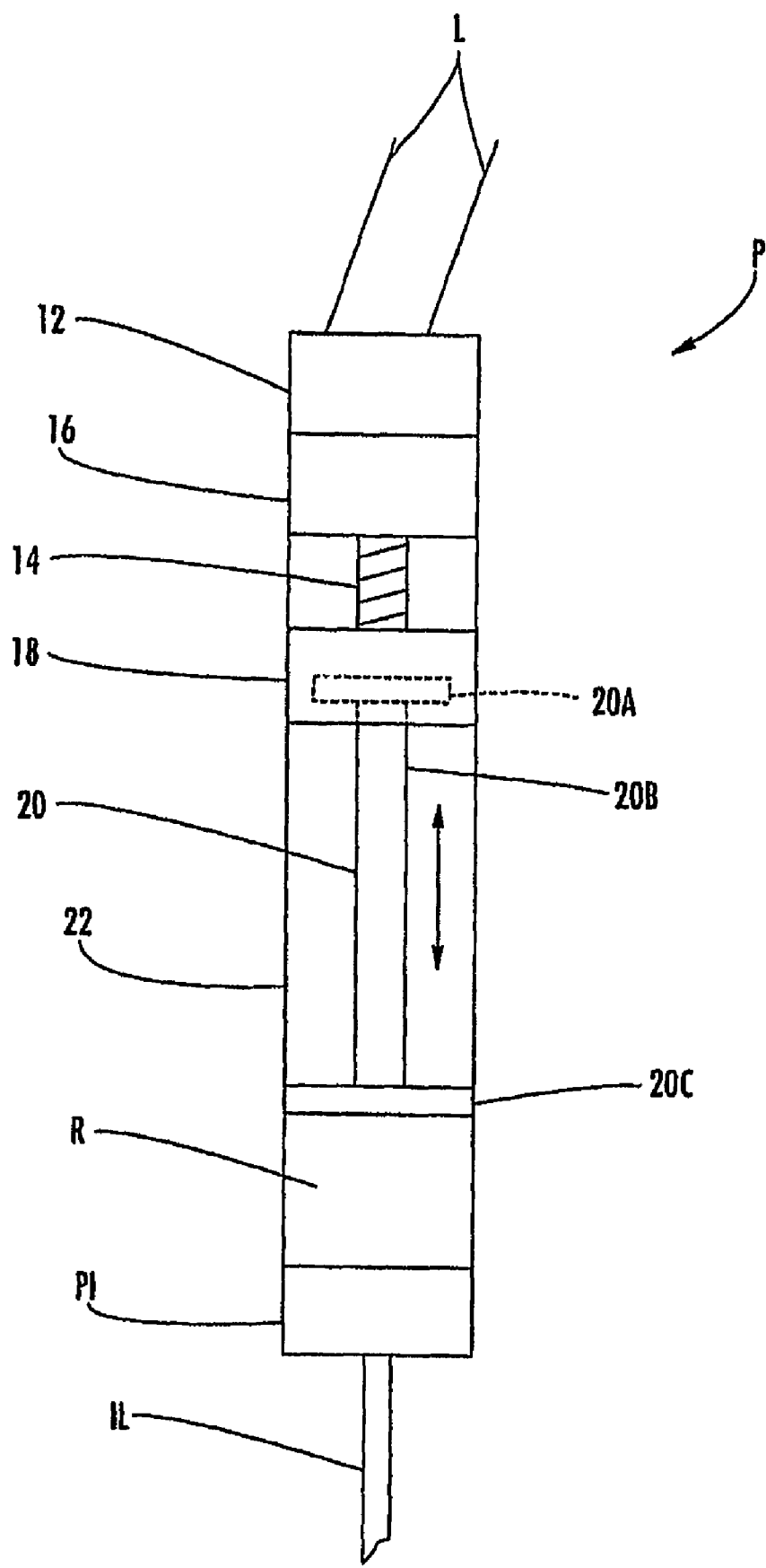
FIG. 2 is a simplified diagram of a linear displacement pump provided in the sample processing apparatus of FIG. 1.

Referring to FIG. 2, an example of a suitable linear displacement pump, generally designated P, is diagrammatically illustrated. Pump P includes a servo motor 12 that is energized and controlled through its connection with any suitable electrical circuitry, which could comprise computer hardware and/or software, via electrical leads L. Alternatively, pump P can include any suitable motor for driving the components of a linear displacement pump. For example, pump P can be a stepper motor. Servo motor 12 drives a rotatable lead screw 14 through a gear reduction device 16. Lead screw 14 engages a linearly translatable pump stage 18. A piston or plunger 20 is coupled to pump stage 18 for linear translation within a pump barrel 22 that stores and contains a reagent R to be introduced into microfluidic chip MFC (FIG. 1). Typically, plunger 20 comprises a head portion 20A, an elongate portion or stem 20B, and a distal end or movable boundary 20C. In operation, reagent R is pushed by movable boundary 20C through pump interconnect PI and into input line IL. The structure of each pump P according to advantageous embodiments is further described hereinbelow with reference to FIGS. 7A-9.

In one exemplary yet non-limiting embodiment, pump barrel 22 is a gas-tight micro-syringe type, having a volume ranging from approximately 10-250 µl. The thread pitch of lead screw 14 can be approximately 80 threads per inch. Gear reduction device 16 produces a gear reduction of 1024:1 or thereabouts. Servo motor 12 and gear reduction device 16 can have an outside diameter of 10 mm or thereabouts. Servo motor 12 uses a 10-position magnetic encoder with quadrature encoding that provides forty encoder counts per revolution, and the resolution is such that each encoder count is equivalent to 0.0077 µm of linear displacement. The foregoing specifications for the components of pump P can be changed without departing from the scope of the embodiment.

Figure 3A:
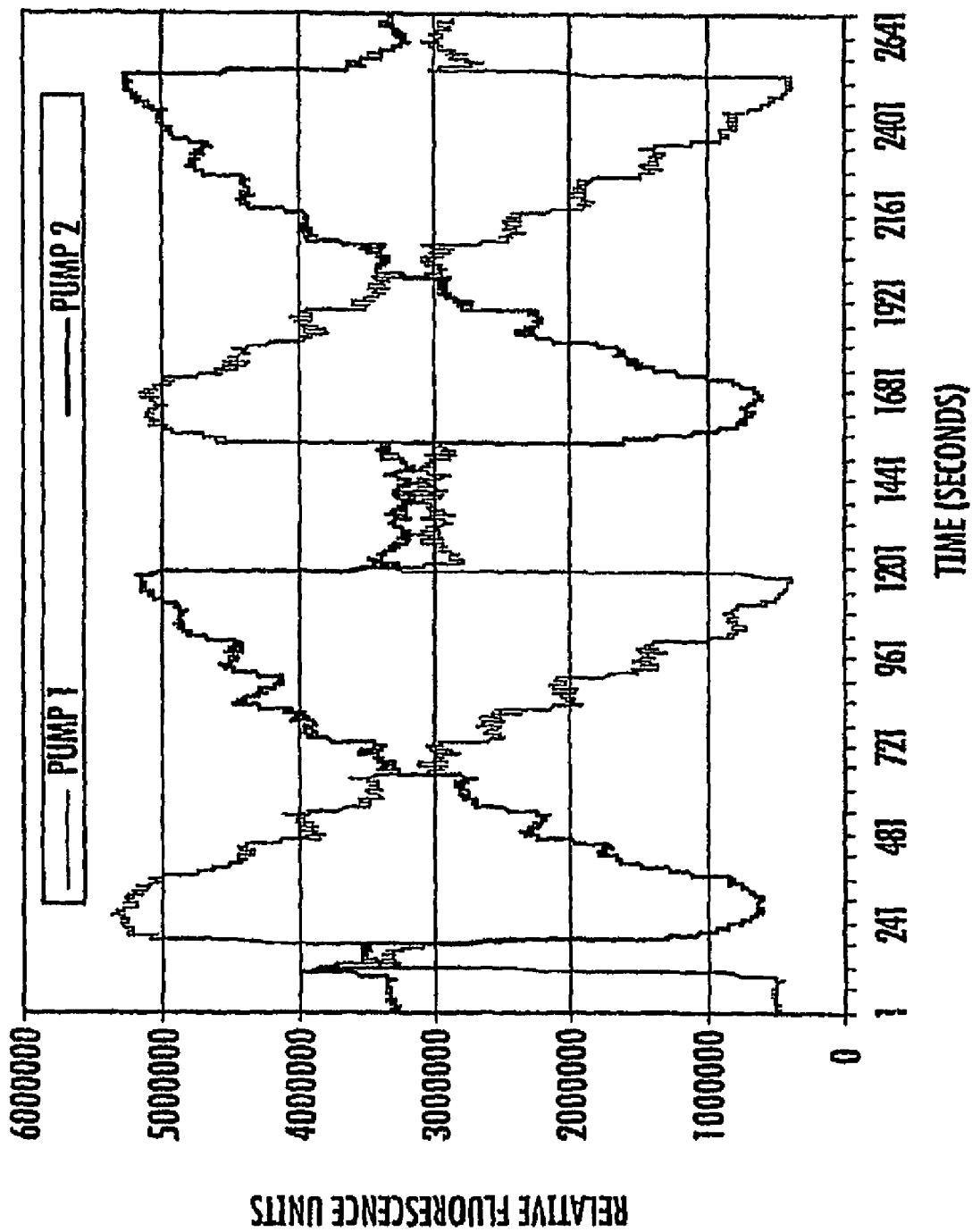
FIG. 3A is a plot of step gradients generated by two pumps, each containing a different fluorophore, and controlled to create steps of 0.1 nl/min ranging from 0.0 to 1.0 nl/min.

In some embodiments for which a plurality of pumps are provided (e.g., pumps $P_A$-$P_C$ in FIG. 1), the respective operations of pumps $P_A$-$P_C$ and thus the volumetric flow rates produced thereby are individually controllable according to individual, pre-programmable fluid velocity profiles. The use of pumps $P_A$-$P_C$ driven by servo motors 12 can be advantageous in that smooth, truly continuous (i.e., non-pulsatile and non-discrete) flows can be processed in a stable manner. In some embodiments, pumps $P_A$-$P_C$ are capable of producing flow rates permitting flow grading between about 0 and 500 nl/min, with a precision of 0.1 nl/min in a stable, controllable manner. Optionally, pumps $P_A$-$P_C$ can produce flow rates permitting flow grading from 0 to as little as 5 nl/min. FIG. 3A is a plot of step gradients generated by two pumps, each containing a different fluorophore, and controlled to create steps of 0.1 nl/min ranging from 0.0 to 1.0 nl/min. The flow in the two pumps were merged in a microfluidic chip and the resulting fluorescence signals were measured to determine the ratio of the mix. The combined flow rate of the two pumps was 1 nl/min, with steps of 0.1 nl/min being made to demonstrate the precision of the flow rate—continuously varying flows also are possible, as described hereinbelow. Moreover, the operation of each servo motor 12 (e.g., the angular velocity of its rotor) can be continuously varied in direct proportion to the magnitude of the electrical control signal applied thereto. In this manner, the ratio of two or more converging streams of reagents (e.g. reagents $R_A$-$R_C$ in FIG. 1) can be continuously varied over time to produce continuous concentration gradients in microfluidic chip MFC. Thus, the number of discrete measurements that can be taken from the resulting concentration gradient is limited only by the sampling rate of the measurement system employed and the noise in the concentration gradient. Moreover, excellent data can be acquired using a minimal amount of reagent. For instance, in the practice of the present embodiment, high-quality data has been obtained from concentration gradients that consumed only 10 nl of reagent (total volume) from three simultaneous flows of reagents $R_A$-$R_C$.

The ability to produce very low flow-rate, stable displacement flows to generate concentration gradients, believed to be 3-4 orders of magnitude slower than that heretofore attainable, provides a number of advantages. Chips can be fabricated from any material, and surface chemistry does not need to be carefully controlled, as with electro-osmotic pumping. Any fluid can be pumped, including fluids that would be problematic for electro-osmotic flows (full range of pH, full range of ionic strength, high protein concentrations) and for pressure driven flows (variable viscosities, non-Newtonian fluids), greatly simplifying the development of new assays. Variations in channel diameters, either from manufacture variability or from clogging, do not affect flow rates, unlike electro-osmotic or pressure flows. Computer control and implementation of control (sensors and actuators) are simpler than for pressure flows, which require sensors and actuators at both ends of the channel. Displacement-driven flows provide the most-straightforward means for implementing variable flows to generate concentration gradients.

The ability to pump at ultra-low flow rates (nl/min) provides a number of advantages in the operation of certain embodiments of microfluidic chip MFC and related methods disclosed herein. These low flow rates enable the use of microfluidic channels with very small cross-sections. Higher, more conventional flow rates require the use of longer channels in order to have equivalent residence times (required to allow many biochemical reactions or biological responses to proceed) or channels with larger cross-sectional areas (which can greatly slow mixing by diffusion and increase dispersion of concentration gradients). In addition, reagent use is decreased because, all other parameters being equal, decreasing the flow rate by half halves the reagent use. Smaller channel dimensions (e.g., 5-30 µm) in the directions required for diffusional mixing of reagents permits even large molecules to rapidly mix in the microfluidic channels.

Referring back to FIG. 1, microfluidic chip MFC comprises a body of material in which channels are formed for conducting, merging, and mixing reagents $R_A$-$R_C$ for reaction, dilution or other purposes. Microfluidic chip MFC can be structured and fabricated according to any suitable techniques, and using any suitable materials, now known or later developed. In advantageous embodiments, the channels of microfluidic chip MFC are formed within its body to prevent evaporation, contamination, or other undesired interaction with or influence from the ambient environment.

Suitable examples of such a microfluidic chip MFC are disclosed in co-pending, commonly owned U.S. Provisional Applications entitled MICROFLUIDIC SYSTEMS, DEVICES AND METHODS FOR REDUCING DIFFUSION AND COMPLIANCE EFFECTS AT A FLUID MIXING REGION, U.S. Provisional Application No. 60/707,220; MICROFLUIDIC SYSTEMS, DEVICES AND METHODS FOR REDUCING NOISE GENERATED BY MECHANICAL INSTABILITIES, U.S. Provisional Application No. 60/707,245; MICROFLUIDIC SYSTEMS, DEVICES AND METHODS FOR REDUCING BACKGROUND AUTOFLUORESCENCE AND THE EFFECTS THEREOF, U.S. Provisional Application No. 60/707,386; and MICROFLUIDIC CHIP APPARATUSES, SYSTEMS, AND METHODS HAVING FLUIDIC AND FIBER OPTIC INTERCONNECTIONS, U.S. Provisional Application No. 60/707,246, the contents of which are incorporated herein in their entireties. As discussed therein, to provide internal channels, microfluidic chip MFC can comprise two body portions such as plates or layers, with one body portion serving as a substrate or base on which features such as channels are formed and the other body portion serving as a cover. The two-body portions can be bonded together by any means appropriate for the materials chosen for the body portions. Non-limiting examples of bonding techniques include thermal bonding, anodic bonding, glass frit bonding, adhesive bonding, and the like. Non-limiting examples of materials used for the body portions include various structurally stable polymers such as polystyrene, metal oxides such as sapphire ($Al_2O_3$), silicon, and oxides, nitrides or oxynitrides of silicon (e.g., $Si_xN_y$, glasses such as $SiO_2$, or the like). In advantageous embodiments, the materials are chemically inert and biocompatible relative to the reagents to be processed, or include surfaces, films, coatings or are otherwise treated so as to be rendered inert and/or biocompatible. The body portions can be constructed from the same or different materials. To enable optics-based data encoding of analytes processed by microfluidic chip MFC, one or both body portions can be optically transmissive or include windows at desired locations. The channels can be formed by any suitable micro-fabricating techniques appropriate for the materials used, such as the various etching, masking, photolithography, ablation, and micro-drilling techniques available. The channels can be formed, for example, according to the methods disclosed in a co-pending, commonly owned U.S. Provisional Application entitled MICROFLUIDIC CHIP APPARATUSES, SYSTEMS, AND METHODS HAVING FLUIDIC AND FIBER OPTIC INTERCONNECTIONS, U.S. Provisional Application No. 60/707,246, the content of which is incorporated herein in its entirety. In some embodiments, the size of the channels can range from approximately 5 to 500 µm in cross-sectional area.

As shown in FIG. 1, as one exemplary fluidic architecture, the channels of microfluidic chip MFC include a first input or pre-mixing channel $IC_A$, a second input or pre-mixing channel $IC_B$, and a third input or pre-mixing channel $IC_C$. Input channels $IC_A$, $IC_B$ and $IC_C$ fluidly communicate with corresponding pumps $P_A$, $P_B$, and $P_C$ via input lines $IL_A$, $IL_B$, and $IL_C$. In some embodiments, input channels $IC_A$, $IC_B$ and $IC_C$ interface with input lines $IL_A$, $IL_B$, and $IL_C$ through respective chip interconnects $CI_A$, $CI_B$ and $CI_C$. Chip interconnects $CI_A$, $CI_B$ and $CI_C$ can be provided in accordance with embodiments disclosed in a co-pending, commonly owned U.S. Provisional Application entitled MICROFLUIDIC CHIP APPARATUSES, SYSTEMS, AND METHODS HAVING FLUIDIC AND FIBER OPTIC INTERCONNECTIONS, U.S. Provisional Application No. 60/707,246, the content of which is incorporated herein in its entirety. In addition to introducing separate reagent streams into microfluidic chip MFC, first and second input channels $IC_A$ and $IC_B$ can serve as temperature-equilibrating channels in which their respective reagents $R_A$ and $R_B$ to be mixed are equilibrated to a given surrounding temperature.

First input channel $IC_A$ and second input channel $IC_B$ terminate or meet at a first T-junction or merging point $MP_1$. From first merging point $MP_1$, a first mixing channel $MC_1$ traverses through microfluidic chip MFC over a distance sufficient to enable passive mixing of reagents $R_A$ and $R_B$ introduced by first input channel $IC_A$ and second input channel $IC_B$. In some embodiments, the mechanism for passive mixing is thermal or molecular diffusion that depends on flow velocity (e.g. time of flight) and distance of travel. Accordingly, microfabricated active mixers, which can be a source of noise, complexity, unreliability and cost are not required but could be provided. In the present exemplary embodiment, third input channel $IC_C$ and first mixing channel $MC_1$ terminate or meet at a second T-junction or merging point $MP_2$, from which a second mixing channel $MC_2$ traverses through microfluidic chip MFC over a distance sufficient for mixing.

Second mixing channel $MC_2$ communicates with a process/reaction channel or aging loop AL. Aging loop AL has a length sufficient for prosecuting a reaction or other interaction between reagents after the reagents have been introduced in two or more of first input channel $IC_A$, second input channel $IC_B$ and/or third input channel $IC_C$, merged at first mixing point $MP_1$ and/or second mixing point $MP_2$, and thereafter mixed in first mixing channel $MC_1$ and/or second mixing channel $MC_2$. For a given area of microfluidic chip MFC, the length of aging loop AL can be increased by providing a folded or serpentine configuration as illustrated in FIG. 1. For many processes contemplated herein, the length of aging loop AL and the linear velocity of the fluid flowing therethrough determines the time over which a reaction can proceed. A longer aging loop AL or a slower linear velocity permits longer reactions. The length of aging loop AL can be tailored to a specific reaction or set or reactions, such that the reaction or reactions have time to proceed to completion over the length of aging loop AL. Conversely, a long aging loop AL can be used in conjunction with measuring shorter reaction times by taking measurements closer to second mixing channel $MC_2$.

As further illustrated in FIG. 1, a detection location or point DP is defined in microfluidic chip MFC at an arbitrary point along the flow path of the reagent mixture, e.g., at a desired point along aging loop AL. More than one detection point DP can be defined so as to enable multi-point measurements and thus permit, for example, the measurement of a reaction product at multiple points along aging loop AL and hence analysis of time-dependent phenomena or automatic localization of the optimum measurement point (e.g., finding a point yielding a sufficient yet not saturating analytical signal). In some methods as further described hereinbelow, however, only a single detection point DP is needed. Detection point DP represents a site of microfluidic chip MFC at which any suitable measurement (e.g., concentration) of the reagent mixture can be taken by any suitable encoding and data acquisition technique. As one example, an optical signal can be propagated though microfluidic chip MFC at detection point DP, such as through its thickness (e.g., into or out from the sheet of FIG. 1) or across its plane (e.g., toward a side of the sheet of FIG. 1), to derive an analytical signal for subsequent off-chip processing. Hence, microfluid chip MFC at detection point DP can serve as a virtual, micro-scale flow cell as part of a sample analysis instrument.

After an experiment has been run and data have been acquired, the reaction products flow from aging loop AL to any suitable off-chip waste site or receptacle W. Additional architectural details and features of microfluidic chip MFC are disclosed in co-pending, commonly owned U.S. Provisional Applications entitled MICROFLUIDIC SYSTEMS, DEVICES AND METHODS FOR REDUCING DIFFUSION AND COMPLIANCE EFFECTS AT A FLUID MIXING REGION, U.S. Provisional Application No. 60/707,220; MICROFLUIDIC SYSTEMS, DEVICES AND METHODS FOR REDUCING NOISE GENERATED BY MECHANICAL INSTABILITIES, U.S. Provisional Application No. 60/707,245; MICROFLUIDIC SYSTEMS, DEVICES AND METHODS FOR REDUCING BACKGROUND AUTOFLUORESCENCE AND THE EFFECTS THEREOF, U.S. Provisional Application No. 60/707,386; and MICROFLUIDIC CHIP APPARATUSES, SYSTEMS, AND METHODS HAVING FLUIDIC AND FIBER OPTIC INTERCONNECTIONS, U.S. Provisional Application No. 60/707,246, the contents of which are incorporated in their entireties.

An example of a method for generating and mixing concentration gradients using sample processing apparatus SPA illustrated in FIG. 1 will now be described. The respective pump barrels 22 (FIG. 2) of two or more of pumps $P_A$-$P_C$ are filled with different reagents $R_A$-$R_C$ and installed in pump assembly PA (FIG. 1). It will be understood, however, that one or more of pumps $P_A$-$P_C$ could be placed in communication with an automated or non-automated liquid handling system to selectively supply reagents $R_A$-$R_C$ as well as buffers, solvents, and the like. Examples of automated liquid handling systems are described hereinbelow with reference to FIGS. 15A-15C. Microfluidic chip MFC, typically with input lines $IL_A$, $IL_B$ and $IL_C$ attached, is mounted to any suitable holder such as a microscope stage as described hereinbelow in conjunction with one particular embodiment. The proximal (upstream) ends of input lines $IL_A$, $IL_B$ and $IL_C$ are attached to the corresponding distal (downstream) ends of pump barrels 22 (FIG. 2), such as by using pump interconnects $PI_A$-$PI_C$ according to certain embodiments disclosed herein. Any suitable method can then be performed to purge the channels of microfluidic chip MFC to remove any contaminants, as well as bubbles or any other compressible fluids affecting flow rates and subsequent concentration gradients. For instance, prior to loading reagents $R_A$-$R_C$ into pump assembly PA, pump assembly PA can be used to run a solvent through microfluidic chip MFC. Any configuration and calibration of the equipment used for detection/measurement can also be performed at this point, including the selection and/or alignment of optical equipment such as the optics described hereinbelow with reference to FIG. 5.

Once sample processing apparatus SPA has been prepared, concentration gradients can be run through microfluidic chip MFC. Two or more of pumps $P_A$, $P_B$ and/or $P_C$ are activated to establish separate flows of different reagents $R_A$, $R_B$ and/or $R_C$ into microfluidic chip MFC for combination, mixing, reaction, and measurement. A variety of combining strategies can be employed, depending on the number of inputs into microfluidic chip MFC and the corresponding number of pumps $P_A$-$P_C$, on their sequence of mixing determined by the geometry of fluidic channels in microfluidic chip MFC, and on the sequence of control commands sent to the pumps $P_A$-$P_C$. Using a microfluidic chip MFC with three inputs as illustrated in FIG. 1, for example, three reagents (reagents $R_A$, $R_B$ and $R_C$) can be input into microfluidic chip MFC, and concentration gradients of reagents $R_A$ versus $R_B$ can then be run against a constant concentration of reagent $R_C$. For another example, by using a four-input microfluidic chip MFC, concentration gradients of reagents $R_A$ and $R_B$ can be run with fixed concentrations of reagent $R_C$ and an additional reagent $R_D$. Due to the small size of the channels of microfluidic chip MFC, reagents $R_A$, $R_B$ and/or $R_C$ mix quickly (e.g., less than one second) in mixing channels $MC_1$ and/or $MC_2$ due to passive diffusion.

In accordance with one embodiment of the method, the total or combined volumetric flow rate established by the active pumps $P_A$, $P_B$ and/or $P_C$ can be maintained at a constant value during the run, in which case the transit time from mixing to measurement is constant and, consequently, the duration of reaction is held constant. In addition, the ratio of the individual flow rates established by respective pumps $P_A$, $P_B$ and/or $P_C$ can be varied over time by individually controlling their respective servo motors 12, thereby causing the resulting concentration gradient of the mixture in aging loop AL to vary with time (i.e. concentration varies with distance along aging loop AL). The concentration gradient of interest is that of the analyte relative to the other components of the mixture. The analyte can be any molecule of interest, and can be any form of reagent or component. Non-limiting examples include inhibitors, substrates, enzymes, fluorophores or other tags, and the like. As the reaction product passes through detection point DP with a varying concentration gradient, the detection equipment samples the reaction product flowing through according to any predetermined interval (e.g., 100 times per second). The measurements taken of the mixture passing through detection point DP can be temporally correlated with the flow ratio produced by pumps $P_A$, $P_B$ and/or $P_C$, and a response can be plotted as a function of time or concentration.

Figure 3B:
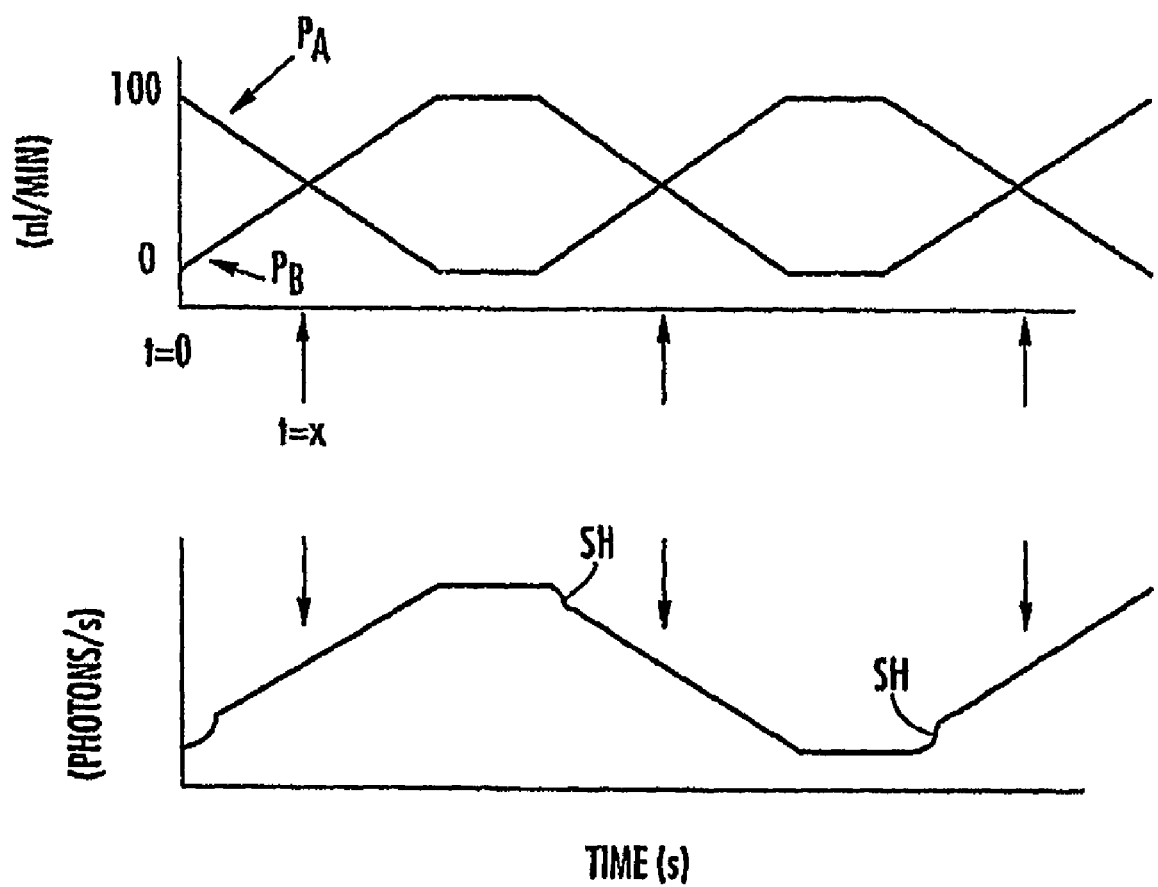
FIG. 3B is a plot of pump-driven flow velocity profiles superimposed over a plot of a measured concentration value resulting from the combination of reagent input streams in accordance with the flow velocity profiles according to embodiments disclosed herein.

Referring to FIG. 3B, an exemplary plot of varying flow velocity profiles programmed for two pumps (e.g., pumps $P_A$ and $P_B$) is given as a function of time, along with the resulting reagent concentration over time. As can be appreciated by persons skilled in the art, the flow velocity profiles can be derived from information generated by encoders typically provided with pumps $P_A$, $P_B$ and $P_C$ that, for example, transduce the angular velocities of their respective servo motors 12 by magnetic coupling or by counting a reflective indicator such as a notch or hash mark. Similarly, a linear encoder can directly measure the movement of plunger 20 or parts that translate with plunger 20. It can be seen that the total volumetric flow rate can be kept constant even while varying concentration gradients over time, by decreasing the flow rate of pump $P_A$ while increasing the flow rate of pump $P_B$. For instance, at time t=0, the flow rate associated with pump $P_A$ has the relative value of 100% of the total volumetric flow rate, and the flow rate associated with pump $P_B$ has the relative value of 0%. As the flow rate of pump $P_A$ is ramped down and the flow rate of pump $P_B$ is ramped up, their respective profile lines cross at time t=x, where each flow rate is 50%. As shown in FIG. 3B, each flow rate can be oscillated between 0% and 100%. The resulting plot of concentration can be obtained, for example, through the use of a photodetector that counts photons per second, although other suitable detectors could be utilized as described hereinbelow. Similarly, non-linear concentration gradients and more complex concentration gradients of reagents $R_A$, $R_B$ and $R_C$ can be generated through appropriate command of the pumps $P_A$, $P_B$ and $P_C$. The trace of fluorescence in FIG. 3B includes apparent steps of "shoulders" SH at the beginning of each increasing gradient and each decreasing gradient. These can arise from such phenomena as stiction in the pump or associated parts, inertia of the motor, poor encoder resolution at rotational velocities near zero, or compliance upstream of a merge point. Shoulders SH are systematic errors in the gradient, and means to minimize these errors are disclosed in co-pending, commonly owned U.S. Provisional Application entitled MICROFLUIDIC SYSTEMS, DEVICES AND METHODS FOR REDUCING DIFFUSION AND COMPLIANCE EFFECTS AT A FLUID MIXING REGION, U.S. Provisional Application No. 60/707,220; and MICROFLUIDIC SYSTEMS, DEVICES AND METHODS FOR REDUCING NOISE GENERATED BY MECHANICAL INSTABILITIES, U.S. Provisional Application No. 60/707,245, the contents of which are incorporated in their entireties.

Sample processing apparatus SPA is useful for a wide variety of applications, due at least in part to the simplicity of the technique for concentration gradient mixing described hereinabove and the ubiquity of concentration gradients in assays. Non-limiting examples of applications include enzyme kinetics, clinical diagnostics for neo-natal care (e.g., blood enzyme diagnostics with microliter samples), toxicity studies for drug development (e.g., P450 assays or S9 fraction assays), flow cytometry, cell-based assays, and gradient elution for mass spectrometry.

Exemplary enzymological variables and measurements that can be analyzed and prepared include, but are not limited to:

(1) basic steady-state kinetic constants, such as Michaelis constants for substrates ($K_m$), maximum velocity ($V_{max}$), and the resultant specificity constant ($V_{max}/K_m$ or $k_{cat}/K_m$);

(2) binding constants for ligands ($K_d$) and capacity of receptor binding ($B_{max}$);

(3) kinetic mechanism of a bi- or multi-substrate enzyme reaction;

(4) effect of buffer components, such as salts, metals and any inorganic/organic solvents and solutes on enzyme activity and receptor binding;

(5) kinetic isotope effect on enzyme catalyzed reactions;

(6) effect of pH on enzyme catalysis and binding;

(7) dose-response of inhibitor or activator on enzyme or receptor activity ($IC_{50}$ and $EC_{50}$ value);

(8) analysis of mechanism of inhibition of an enzyme catalyzed reaction and associated inhibition constants (slope inhibition constant ($K_{is}$) and intercept inhibition constant ($K_{ii}$));

(9) equilibrium binding experiments to determine binding constants ($K_d$); and

(10) determination of binding stoichiometry via a continuous variation method.

The amount of data points and accuracy of collection for the above noted exemplary applications, when performed using the sample processing apparatus SPA described herein, are superior to that observed in any heretofore known data collection techniques. In particular, the sample processing apparatus SPA provides directly measurable continuous concentration gradients by accurately varying the volumetric flow rates of multiple reagent streams simultaneously by a precisely known amount. Therefore, it is known by direct observation what the expected concentration gradients are, rather than having to calculate the gradients indirectly. This allows for more accurate data collection than is possible with previously described devices for the applications listed above and others. The pump mechanisms described herein facilitate the use of continuous concentration gradients, in that in one embodiment, the pump mechanisms operate by flow displacement, which provides more precise volume control.

Figure 4:
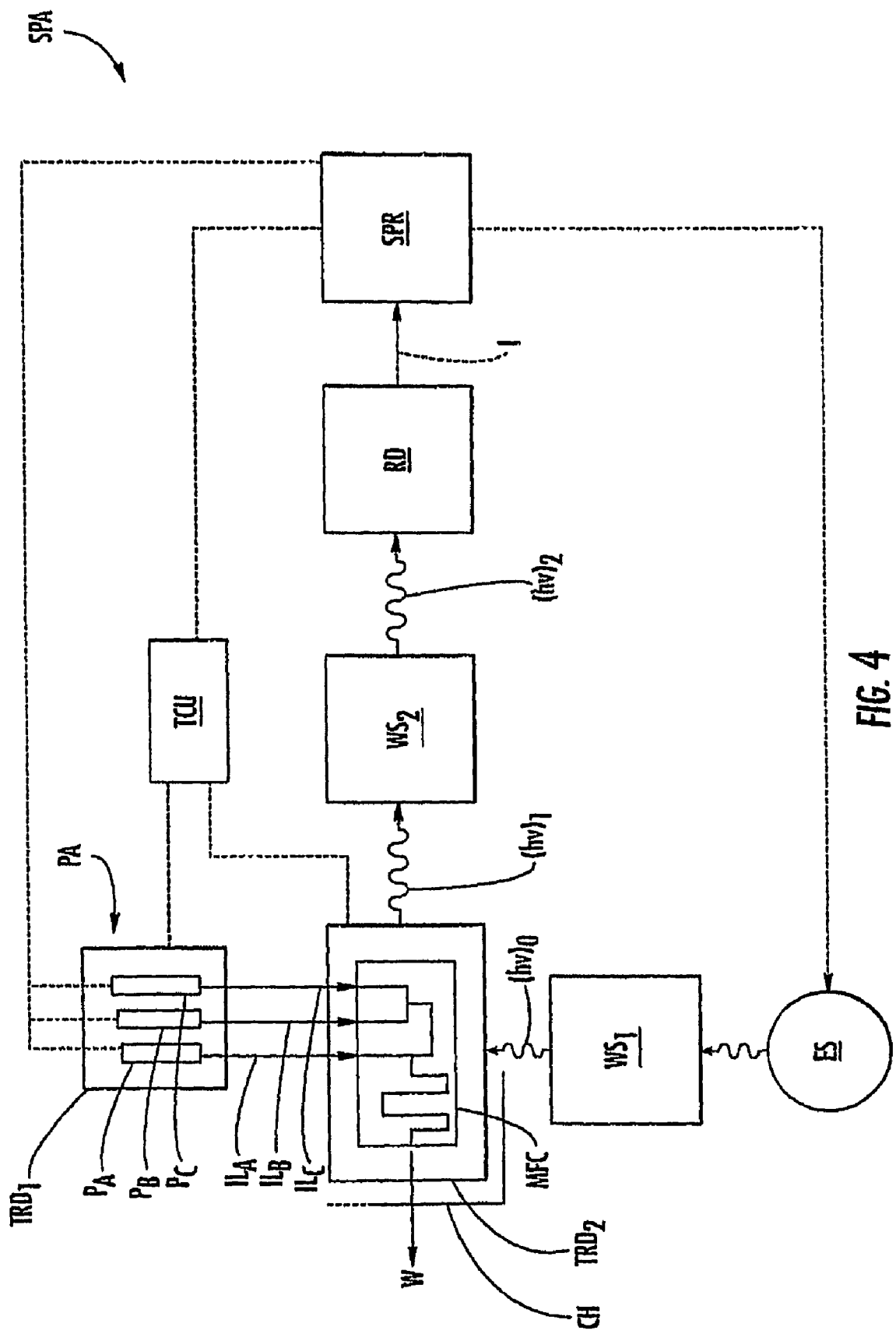
FIG. 4 is a schematic view of a sample processing apparatus with sample measurement components integrated therein according to embodiments disclosed herein.

Referring now to FIG. 4, a generalized schematic of sample processing apparatus SPA is illustrated to show by way of example the integration of other useful components for analytical testing and data acquisition according to spectroscopic, spectrographic, spectrometric, or spectrophotometric techniques, and particularly UV or visible molecular absorption spectroscopy and molecular luminescence spectrometry (including fluorescence, phosphorescence, and chemiluminescence). In addition to pump assembly PA and microfluidic chip MFC, which at detection point DP (FIG. 1) could be considered as serving as a data encoding or analytical signal generating virtual sample cell or cuvette, sample processing apparatus SPA can include an excitation source ES, one or more wavelength selectors $WS_1$ and $WS_2$ or similar devices, a radiation detector RD, and a signal processing and readout device SPR. The particular types of these components and their inclusion with sample processing apparatus SPA can depend on, for example, the type of measurement to be made and the type of analytes to be measured/detected. In some embodiments, sample processing apparatus SPA additionally comprises a thermal control unit or circuitry TCU that communicates with a pump temperature regulating device $TRD_1$ integrated with pump assembly PA for regulating the temperature of the reagents residing in pumps $P_A$-$P_C$, and/or a chip temperature regulating device $TRD_2$ in which microfluidic chip MFC can be enclosed for regulating the temperature of reagents and mixtures flowing therein. Details of these temperature regulating components according to specific embodiments are given hereinbelow. Additionally, a chip holder CH can be provided as a platform for mounting and positioning microfluidic chip MFC, with repeatable precision if desired, especially one that is positionally adjustable to allow the user to view selected regions of microfluidic chip MFC and/or align microfluidic chip MFC (e.g., detection point DP thereof) with associated optics.

Generally, excitation source ES can be any suitable continuum or line source or combination of sources for providing a continuous or pulsed input of initial electromagnetic energy $(hv)_0$ to detection point DP (FIG. 1) of microfluidic chip MFC. Non-limiting examples include lasers, such as visible light lasers including green HeNe lasers, red diode lasers, and frequency-doubled Nd:YAG lasers or diode pumped solid state (DPSS) lasers (532 nm); hollow cathode lamps; deuterium, helium, xenon, mercury and argon arc lamps; xenon flash lamps; quartz halogen filament lamps; and tungsten filament lamps. Broad wavelength emitting light sources can include a wavelength selector $WS_1$ as appropriate for the analytical technique being implemented, which can comprise one or more filters or monochromators that isolate a restricted region of the electromagnetic spectrum. Upon irradiation of the sample at detection point DP, a responsive analytical signal having an attenuated or modulated energy $(hv)_1$ is emitted from microfluidic chip MFC and received by radiation detector RD. Any suitable light-guiding technology can be used to direct the electromagnetic energy from excitation source ES, through microfluidic chip MFC, and to the remaining components of the measurement instrumentation. In some embodiments, optical fibers are employed. The interfacing of optical fibers with microfluidic chip MFC according to advantageous embodiments is disclosed in a co-pending, commonly owned U.S. Provisional Application entitled MICROFLUIDIC CHIP APPARATUSES, SYSTEMS, AND METHODS HAVING FLUIDIC AND FIBER OPTIC INTERCONNECTIONS, U.S. Provisional Application No. 60/707,246, the contents of which are incorporated herein in its entirety. In some embodiments, a miniaturized dip probe can be employed at detection point DP, in which both the optical sending and returning fibers enter the same side of microfluidic chip MFC and a reflective element routes the optical signal down the sending fiber back through the microfluidic channel to the returning fiber. Similarly a single fiber can be used both to introduce the light and to collect the optical signal and return it to a detector. For example, the excitation light for a fluorophore can be introduced into the microfluidic chip by an optical fiber, and the fluorescent light emitted by the sample in the microfluidic chip can be collected by that same fiber and transmitted to a photodetector, with appropriate wavelength selectors permitting rejection of excitation light at the photodetector.

Wavelength selector $WS_2$ is utilized as appropriate for the analytical technique being implemented, and can comprise one or more filters or monochromators that isolate a restricted region of the electromagnetic spectrum and provide a filtered signal $(hv)_2$ for subsequent processing. Radiation detector RD can be any appropriate photoelectric transducer that converts the radiant energy of filtered analytical signal $(hv)_2$ into an electrical signal I suitable for use by signal processing and readout device SPR. Non-limiting examples include photocells, photomultiplier tubes (PMTs), avalanche photodiodes (APDs), photodiode arrays (PDAs), and charge-coupled devices (CCDs). In particular, for fluorescence measurements, a PMT or APD can be operated in a photon counting mode to increase sensitivity or yield improved signal-to-noise ratios. Advantageously, radiation detector RD is enclosed in an insulated and opaque box to guard against thermal fluctuations in the ambient environment and keep out light.

Signal processing and readout device SPR can perform a number of different functions as necessary to condition the electrical signal for display in a human-readable form, such as amplification (i.e., multiplication of the signal by a constant greater than unity), phase shifting, logarithmic amplification, ratioing, attenuation (i.e., multiplication of the signal by a constant smaller than unity), integration, differentiation, addition, subtraction, exponential increase, conversion to AC, rectification to DC, comparison of the transduced signal with one from a standard source, and/or transformation of the electrical signal from a current to a voltage (or the converse of this operation). In addition, signal processing and readout device SPR can perform any suitable readout function for displaying the transduced and processed signal, and thus can include a moving-coil meter, a strip-chart recorder, a digital display unit such as a digital voltmeter or CRT terminal, a printer, or a similarly related device. Finally, signal processing and readout device SPR can control one or more other components of sample processing apparatus SPA as necessary to automate the mixing, sampling/measurement, and/or temperature regulation processes of the methods disclosed herein. For instance, signal processing and readout device SPR can be placed in communication with excitation source ES, pumps $P_A$-$P_C$ and thermal control unit TCU via suitable electrical lines to control and synchronize their respective operations, as well as receive feedback from the encoders typically provided with pumps $P_A$-$P_C$.

As appreciated by persons skilled in the art, the signal processing, readout, and system control functions can be implemented in individual devices or integrated into a single device, and can be implemented using hardware (e.g., a $P_C$ computer), firmware (e.g., application-specific chips), software, or combinations thereof. The computer can be a general-purpose computer that includes a memory for storing computer program instructions for carrying out processing and control operations. The computer can also include a disk drive, a compact disk drive, or other suitable component for reading instructions contained on a computer-readable medium for carrying out such operations. In addition to output peripherals such as a display and printer, the computer can contain input peripherals such as a mouse, keyboard, barcode scanner, light pen, or other suitable component known to persons skilled in the art for enabling a user to input information into the computer.

Figure 5:
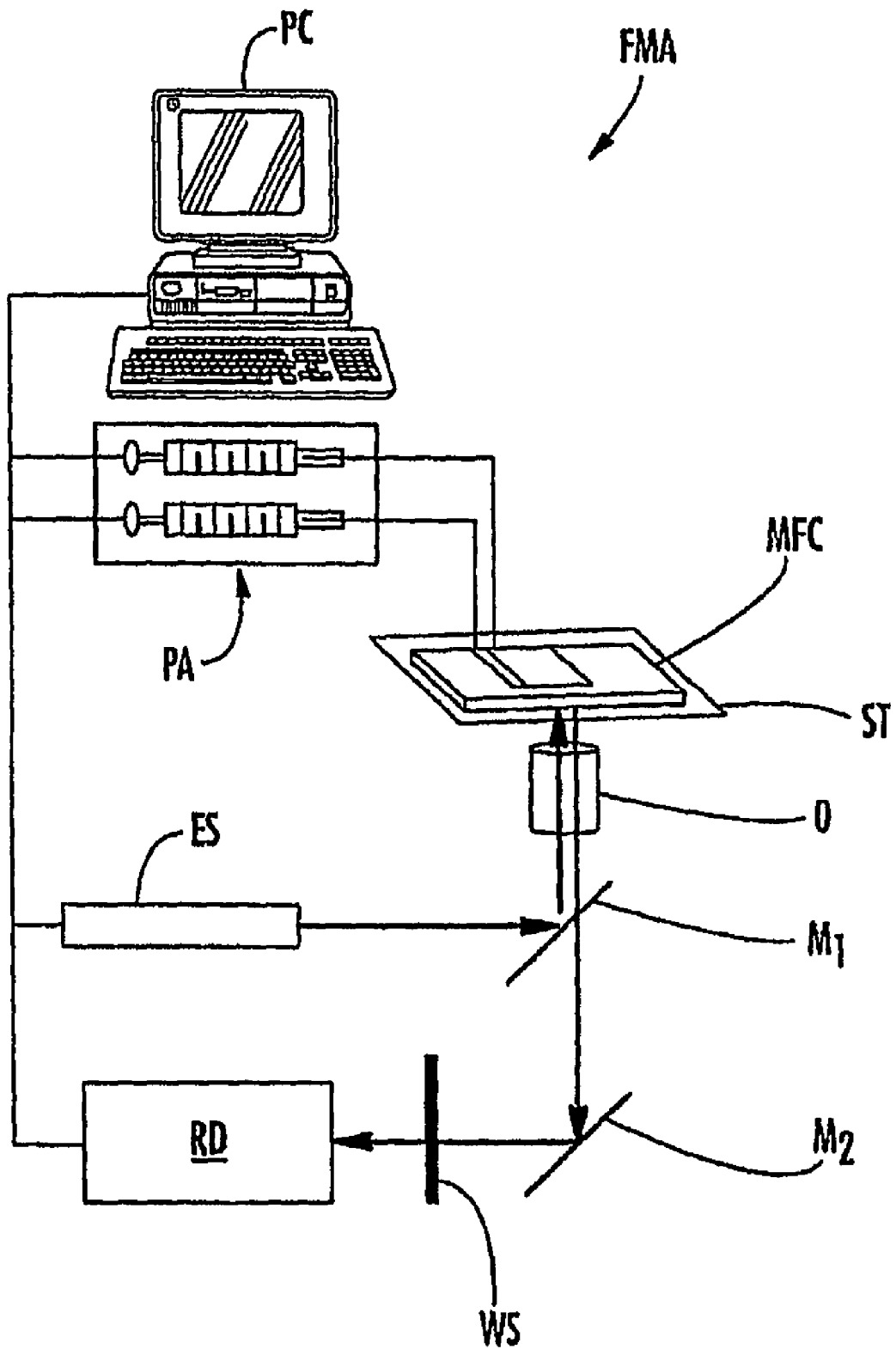
FIG. 5 is a schematic view of a fluorescence measurement apparatus provided in accordance with embodiments disclosed herein.

Referring now to FIG. 5, a specific embodiment of sample processing apparatus SPA is illustrated in the form of a fluorescence measurement apparatus, generally designated FMA, which can be used to measure/detect fluorescence intensity, fluorescence polarization, or time-resolved fluorescence. A microscope, and particularly a fluorescence microscope, can be employed for a number of functions. Microfluidic chip MFC can be mounted on a microscope stage ST typically provided with the microscope. In some embodiments, microscope stage ST can be controllably actuated in X-Y or X-Y-Z space to align microfluidic chip MFC with an objective O of the microscope as well as other associated optics. In addition to enabling a selected area of microfluidic chip MFC to be viewed, objective O can focus or direct incoming light supplied from excitation source ES. Light-guiding optical components can be employed, including a dichroic mirror $M_1$ for reflecting the light from excitation source ES and transmitting the fluorescence signal from microfluidic chip MFC, and an additional mirror $M_2$ if needed for reflecting the attenuated signal to wavelength selector WS.

Fluorescence measuring apparatus FMA can be configured such that multiple excitation wavelengths are simultaneously introduced into a sample containing multiple signal fluorophores inside microfluidic chip MFC. This can be done by using a multiple bandpass filter as a wavelength selector $WS_1$ or by using multiple lasers as excitation light sources. Similarly multiple bandpass dichroic mirrors and multiple wavelength selectors $WS_2$ can be used to transmit the fluorescence from individual fluorophores to multiple signal processing and readout devices SPR.

In the embodiment illustrated in FIG. 5, mirror $M_1$ is a shortpass dichroic reflector that reflects light from excitation source ES and transmits fluorescent light collected from microfluidic chip MFC by objective O back toward radiation detector RD. Wavelength selector WS is a barrier filter appropriate for use in conjunction with a radiation detector RD provided in the form of a photon counter. As further illustrated in FIG. 5, the signal processing and readout device SPR is provided in the form of any suitable computer $P_C$. A suitable computer program, developed for instance using LABVIEW® software, available from National Instruments Corporation, Austin, Tex., can be stored and/or loaded into computer $P_C$ to enable computer $P_C$ to be specifically programmed to control the operation of fluorescence measurement apparatus FMA.

Referring to FIG. 6, an advantageous system control program SCP is depicted for controlling sample processing apparatus SPA generally illustrated in FIG. 4, according to any specific embodiment thereof such as fluorescence measurement apparatus FMA illustrated in FIG. 5. System control program SCP can include five software modules or routines: a configuration module 52, a thermal control module 54, a manual or debug module 56, chip navigating module 58, and a run or data acquisition module 60. As can be appreciated by persons skilled in the art, system control program SCP can be provided as a computer program product, especially one compatible with a graphical user interface (GUI), comprising computer-executable instructions and/or data embodied in a computer-readable medium.

Configuration module 52 enables a user to create individual volumetric flow profiles (see, e.g., FIG. 3B) by which respective pumps $P_A$-$P_C$ of pump assembly PA (see, e.g., FIGS. 1 and 4) are to be controlled for a given experiment. For example, the user can create flow velocity profiles as percentages of a defined total flow rate, as shown in FIG. 3B. Configuration module 52 can include a flag that alerts the user when the individual flow rates do not add up to the total flow rate (i.e., 100%).

Thermal control module 54 controls the operation of thermal control unit TCU (FIG. 4) and thus pump temperature regulating device $TRD_1$ and/or chip temperature regulating device $TRD_2$. Thermal control module 54 can be used, for example, for dictating whether pump temperature regulating device $TRD_1$ and/or chip temperature regulating device $TRD_2$ are to be active during the experiment, providing the set point temperature for pump temperature regulating device $TRD_1$ and/or chip temperature regulating device $TRD_2$, and logging instantaneous temperatures sensed by pump temperature regulating device $TRD_1$ and/or chip temperature regulating device $TRD_2$ to a data file at a user-defined temperature sampling rate.

Manual or debug module 56 can be used to manually control (including, for instance, overriding certain automated functions on an as-needed basis) any aspect of sample processing apparatus SPA. As examples, the user can control the flow rate of each pump $P_A$, $P_B$ and $P_C$ individually, adjust the temperature settings of pumps $P_A$-$P_C$ and microfluidic chip MFC, view in real time the values read by radiation detector RD, monitor any peripheral analog input devices such as photodiodes or thermistors, and the like.

Chip navigation module 58 is a tool for controlling the user's view of microfluidic chip MFC and events occurring therein during an experiment. For instance, chip navigation module 58 can allow the user to define an exact point or region of interest on microfluidic chip MFC and repeatably return to that point or region with the click of a button on the user interface, even after microfluidic chip MFC has been removed from and placed back on chip positioning or mounting stage (FIG. 4) such as microscope stage ST (FIG. 5). The user can automatically cycle through different detection spots if desired. As appreciated by persons skilled in the art, the user's view of microfluidic chip MFC can be effected by any suitable means, such as via a peripheral display device (e.g., CRT screen) provided with computer $P_C$ and using a CCD camera incorporated with the system for viewing microfluidic chip MFC. The views made by the user during an experiment can be recorded into a data file if desired to add a visual component to the analytical process.

Finally, run or data acquisition module actually executes the experiment according to the various user-defined parameters, including the flow velocity profiles designed using configuration module 52 and set point data inputted using thermal control module 54. Moreover, run or data acquisition module 60 can provide a display of information yielded during the course of the experiment, such as flow velocities and responses as described hereinabove with reference to FIG. 3B. The user can watch in real time as data are collected from radiation detector RD, the encoders provided with pumps $P_A$-$P_C$, pump temperature regulating device $TRD_1$, chip temperature regulating device $TRD_2$, and any other analog or digital data-generating devices provided with sample processing apparatus SPA. It will be understood that some of the data can be acquired according to respective, user-defined sampling rates, while other data can be acquired continuously or on-demand.

Figure 7A:
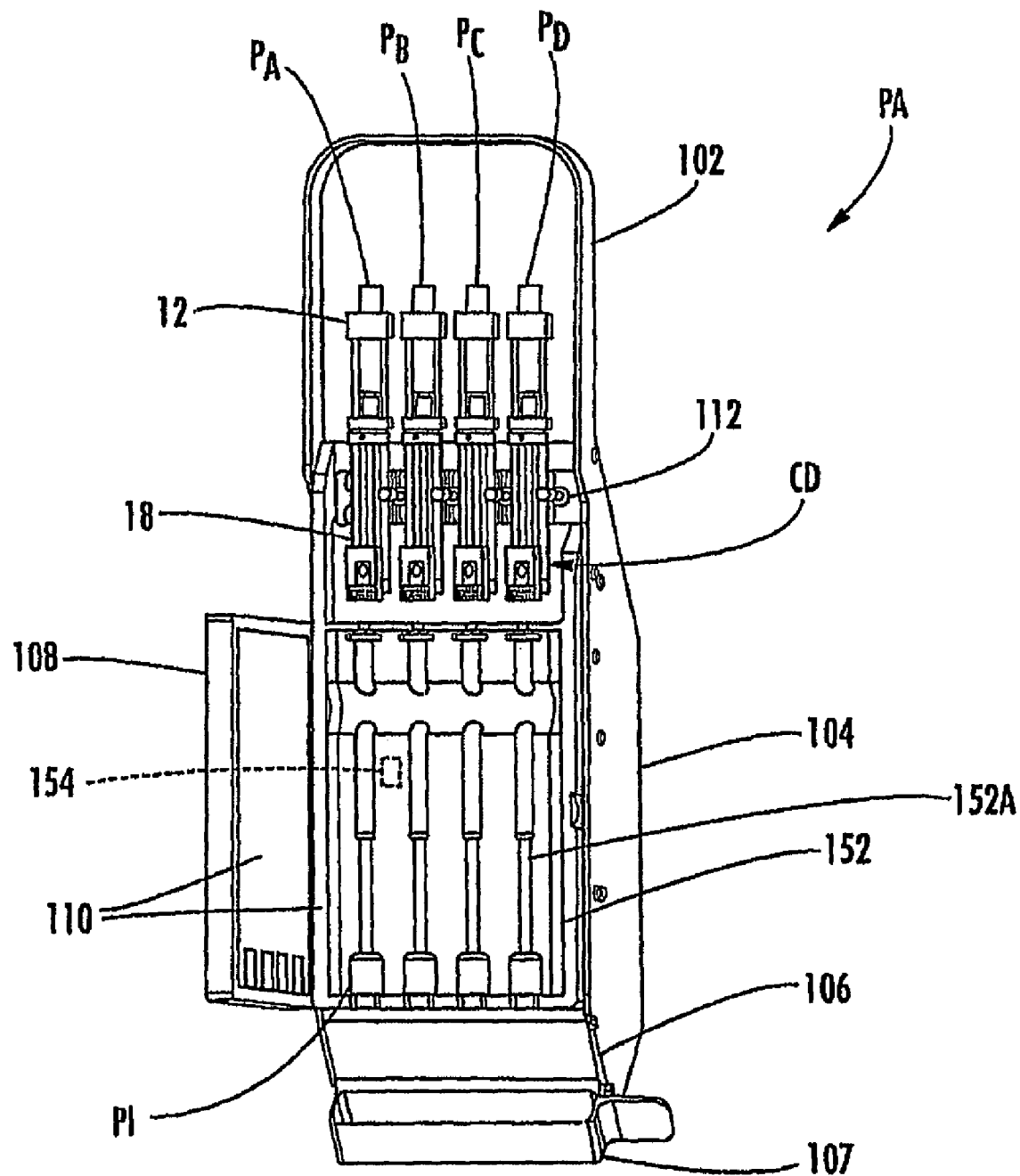
FIGS. 7A and 7B are perspective front and rear views, respectively, of a pump assembly provided in accordance with embodiments disclosed herein.
Figure 7B:
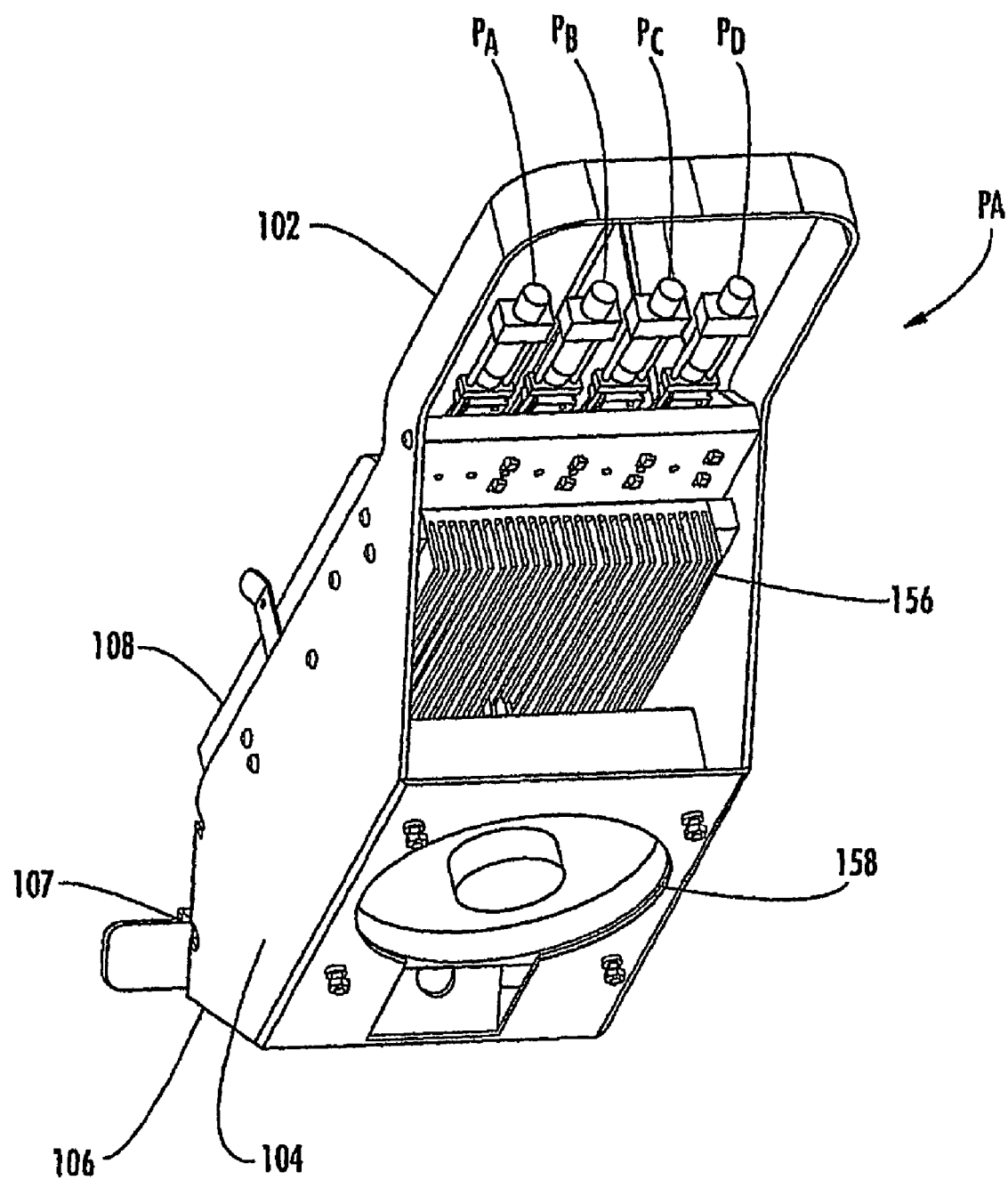
Figure 7C:
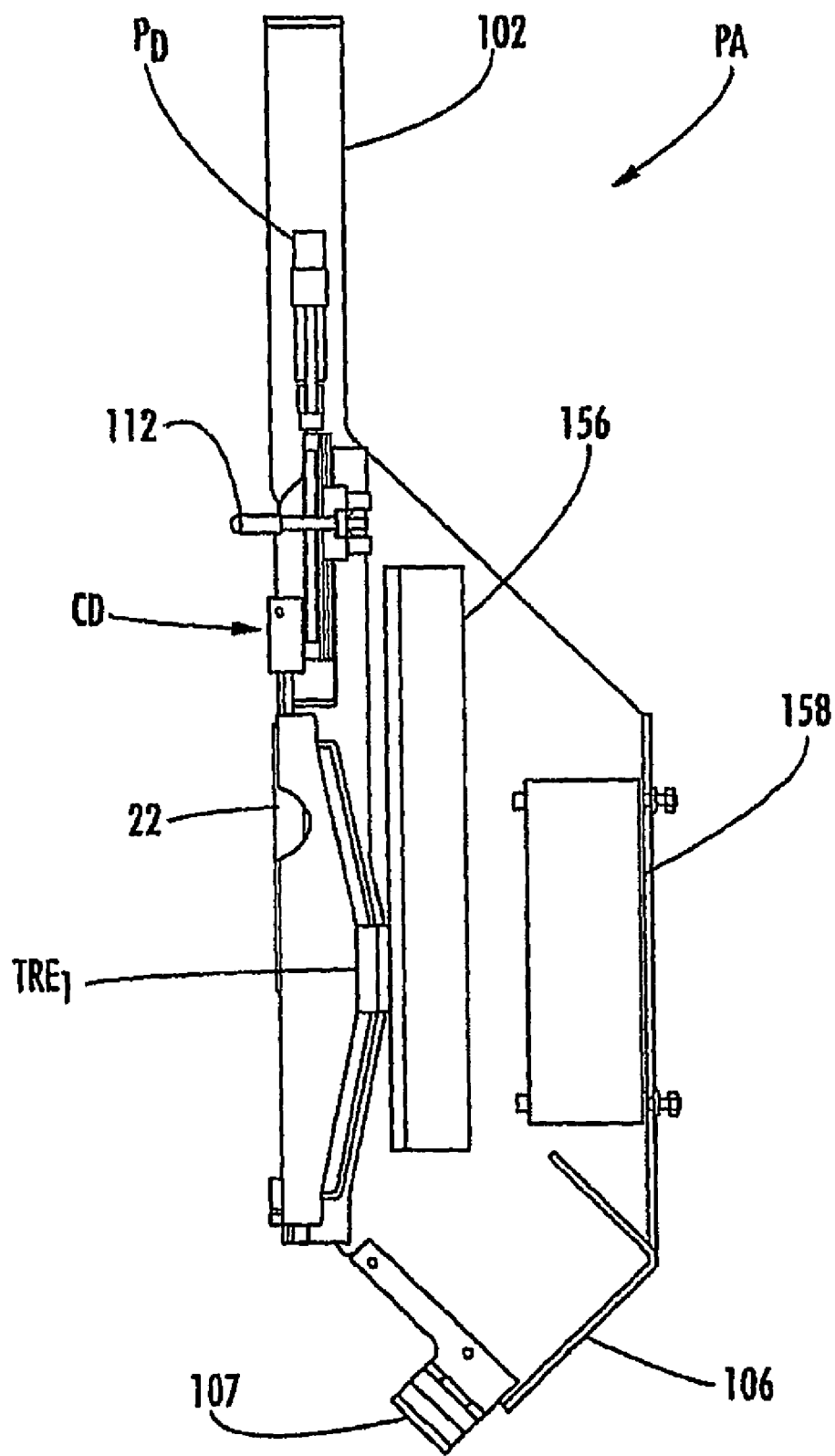
FIG. 7C is a side elevation cut-away view of the pump assembly illustrated in FIGS. 7A and 7B.

Referring now to FIGS. 7A-7C, one exemplary embodiment of pump assembly PA is illustrated that is capable of precisely delivering liquids into microfluidic chip MFC at nl/min-scale, smooth, non-pulsatile flow rates as described hereinabove. Pump assembly PA can include one or more pumps, such as four pumps $P_A$-$P_D$ as illustrated. The various components of each pump $P_A$-$P_D$, described hereinabove and schematically illustrated in FIG. 2, are supported in a pump housing 102 with pump barrels 22 (FIG. 2) being mounted in recesses 152A in a barrel holder 152. Pump housing 102 can be constructed from any suitable material, with non-limiting examples being polyoxymethylene, aluminum, steel, DELRIN® material, or polyvinylchloride. Pump housing 102 can include a stand portion 104 for mounting pump P at a desired angle relative to the vertical to reduce the footprint of pump assembly PA and protect servo motors 12 from condensation resulting from cooling as described hereinbelow. Pump housing 102 can also include a mounting portion 106 such as a bracket for affixing pump assembly PA in place. Preferably, a drip cup 107 is included to catch condensation and serve as a windscreen to prevent input lines IL (see, e.g., FIG. 2) from blowing around, especially when a cooling fan 158 (FIGS. 7B and 7C) is provided to remove heat from a Peltier device or other temperature regulating element $TRE_1$ (see, e.g., FIG. 7C) that cools pump housing 102. Pump housing 102 can include a hinged door 108 to provide access to pump barrels 22 mounted in recesses 152A for replacement or cleaning, or manual loading of reagents therein. The lower portions of pump housing 102 surrounding pump barrels 22, including the inside of door 108 and surrounding barrel holder 152, can be provided with insulation 110 to thermally isolate pump barrels 22 and their contents. To accommodate different positions of plunger 20, the axial positions of pump stages 18 relative to their respective pump barrels 22 (not depicted here, but mounted in recesses 152A in barrel holder 152) can be adjusted through the use of thumb screws 112 or other appropriate fastening or tightening means. Manipulation of thumb screws 112 can release their respective pump stages 18 to allow servo motors 12 to slide up and down while the positions of the pump barrels are fixed by recesses 152A in barrel holder 152.

Figure 8:
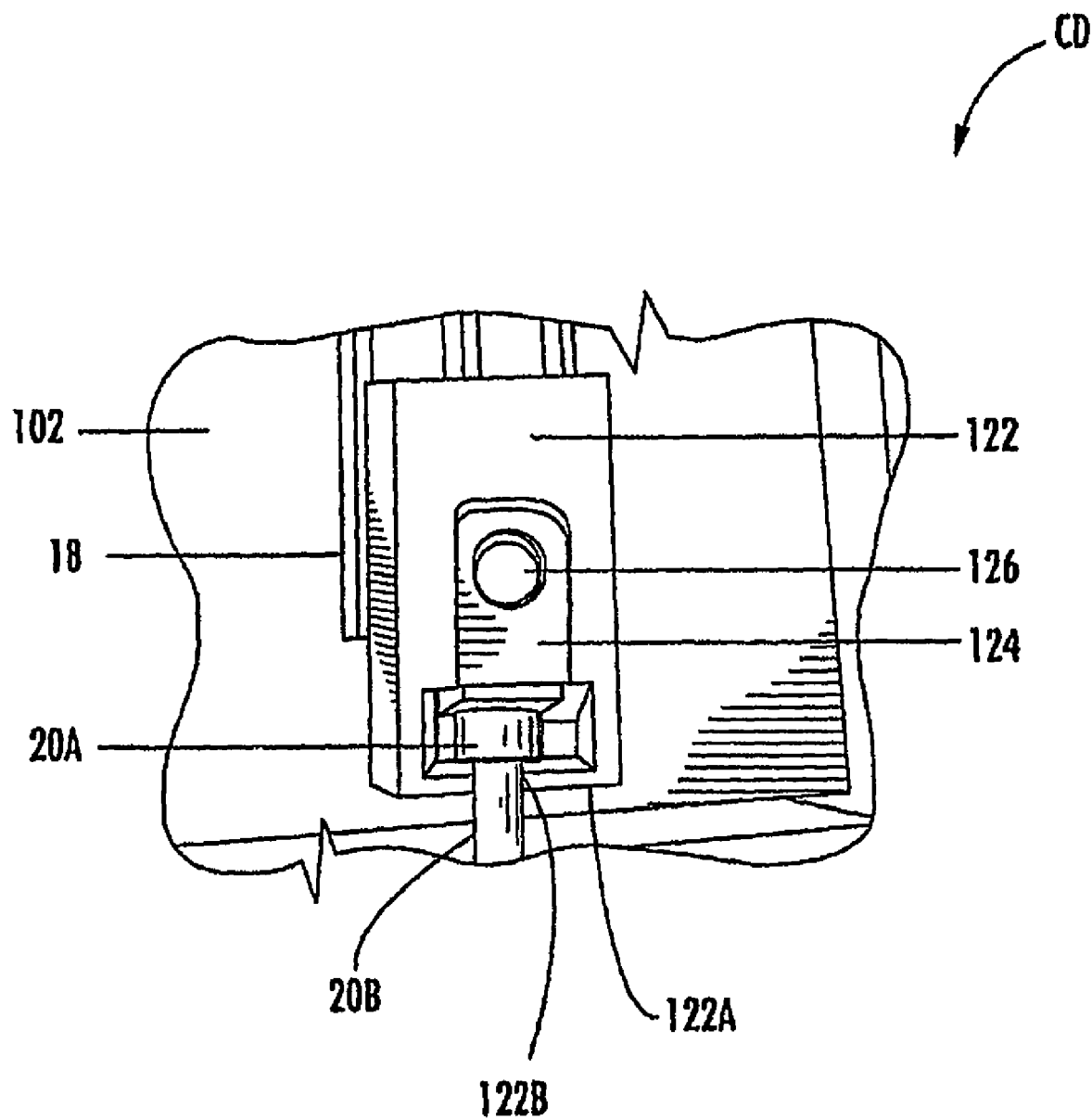
FIG. 8 is a perspective view of a coupling device provided with the pump assembly illustrated in FIGS. 7A, 7B and/or 7C in accordance with embodiments disclosed herein.

Referring to FIG. 8, in one embodiment, each plunger 20 (shown in FIG. 7A) is coupled to its respective pump stage 18 for linear translation therewith by means of a coupling device, generally designated CD. Coupling device CD comprises a plunger clasp 122, a tightening plate 124, and a set screw 126. Plunger clasp 122 is secured to pump stage 18, and includes a cavity 122A and an aperture or recess 122B through which plunger 20 extends. Head portion 20A of plunger 20, which typically has a greater diameter than its stem 20B, is removably disposed in cavity 122A. Set screw 126 extends through a hole of tightening plate 124 and is threaded into pump stage 18. Tightening plate 124 resides in cavity 122A and can be adjusted via set screw 126 to secure head portion 20A of plunger 20 between tightening plate 124 and an inside surface of cavity, thereby effecting a coupling relation between pump stage 18 and plunger 20 with minimal mechanical loss and minimal lateral motion of plunger 20.

In advantageous embodiments, pump assembly PA provides temperature-control functionality. While both heating and cooling can be effected, the ability to cool pump assembly PA is particularly advantageous as it enables thermally labile reagents to be cooled in-situ to prevent their degradation, thereby eliminating the need for ex-situ or on-chip refrigeration. Proteins, for example, can denature at room temperatures in a matter of hours. Thus, cooling is particularly important when lengthy run times are contemplated. For example, if a 10-µl barrel is used, approximately 8 hours of run time is possible at a flow rate of 20 nl/min. In one embodiment, pump assembly PA can maintain a reagent temperature ranging from approximately −4° C. to 70° C. to within 0.05° C. of accuracy. Moreover, thermal control of pump assembly PA provides the flow stability and noise reduction needed when operating at flow rates in the nl/min range. A change in room temperature can cause thermal expansion of the components of pump assembly PA that interact with the liquids being conveyed, thereby causing a thermal pumping effect. For example, when pumping at a low flow rate such as a few nl/min, a 1-nl change in the volume of the system (i.e., 0.01 percent of total volume for a 10 µl syringe pump) over one minute will be noticeable. Similarly, a 1° C. change in the temperature of the stainless steel plunger of some microsyringes causes the plunger to change length by 2 µm, changing the volume inside the microsyringe by 0.3 nl. Because room temperature is a disturbance, thermal pumping appears as noise in the output of the pumps of pump assembly PA. Hence, controlling the temperature of pump assembly PA reduces this noise. Finally, with regard to the multi-pump configuration illustrated in FIGS. 7A-7C, the ability to regulate all pumps $P_A$-$P_D$ at the same temperature reduces any disparity in any temperature gradients respectively existing between each pump $P_A$-$P_D$. Otherwise, the existence of different temperature gradients between pumps $P_A$-$P_D$ can cause pumps $P_A$-$P_D$ to thermally pump out of phase with each other, which can also contribute to signal noise.

As illustrated in FIGS. 7A-7C, pump assembly PA can include a pump temperature regulating device $TRD_1$ (FIG. 4) comprising, in addition to insulated pump housing 102: a barrel holder 152 (FIG. 7A); one or more temperature sensing devices 154 (FIG. 7A); a temperature regulating element, generally designated $TRE_1$ (FIG. 7C); a heat sink 156 (FIGS. 7B and 7C); and a cooling fan 158 (FIGS. 7B and 7C). Barrel holder 152 is mounted within pump housing 102 to support pump barrels 22. To maximize thermal contact between barrel holder 152 and pump barrels 22, elongate recesses 152A are formed in barrel holder 152 that generally conform to the outer profiles of pump barrels 22 for maximum surface contact. Barrel holder 152 can be constructed from any suitably efficient thermally conductive material such as aluminum, copper, or the like. Temperature sensing device 154 is embedded or otherwise placed in thermal contact with barrel holder 152 by any securement means such as thermally conductive epoxy, thermally conducting grease, or simply by direct contact. Temperature sensing device 154 provides real-time temperature feedback for thermal control unit TCU (FIG. 4). Thus, temperature sensing device 154 can be any suitable device such as a thermistor. Heat sink 156 is mounted to pump housing 102 or to barrel holder 152, or is otherwise in thermal contact with the side of barrel holder 152 opposite to pump barrels 22. Heat sink 156 can be employed to dissipate heat during cooling operations, and thus can include cooling fins to maximize the surface area available for heat transfer as appreciated by persons skilled in the art. Additional cooling can be effected through the use of cooling fan 158 if desired or needed. In the illustrated embodiment, cooling fan 158 is mounted at the side of heat sink 156 opposite to barrel holder 152. Similarly, heat can be removed by a water-filled heat exchanger in communication with an external water bath. For instance, heat sink 156 can be configured for circulating water or another suitable heat transfer medium therethrough.

Figure 9:
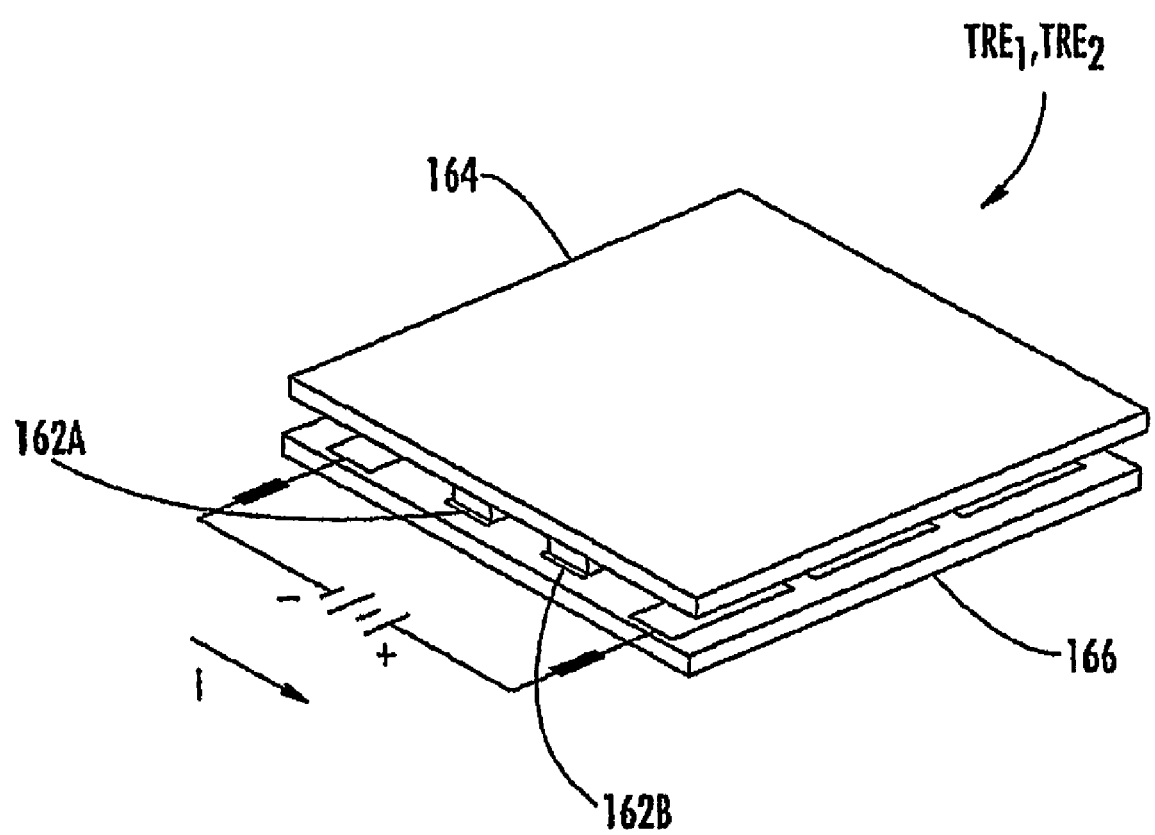
FIG. 9 is a perspective view of a temperature regulating element provided in accordance with embodiments disclosed herein.

Temperature regulating element $TRE_1$ is mounted between barrel holder 152 and heat sink 56 for either transferring heat to barrel holder 152 (and thus barrel and its fluid contents) or transferring heat away from barrel holder 152 to heat sink 156. In advantageous embodiments, temperature regulating element $TRE_1$ is a thermoelectric device such as a Peltier device, as illustrated in FIG. 9, which includes adjoining metals 162A and 162B of different compositions sandwiched between a cold-side plate 164 adjacent to heat sink 156 plate and a hot-side plate 166 adjacent to barrel holder 152. Cold-side plate 164 and hot-side plate 166 are typically of ceramic construction. As appreciated by persons skilled in the art, the passage of current in a reversible direction across the junction of differing metals 162A and 162B, across which a Peltier voltage exists, causes either an evolution or absorption of heat. More specifically, when current is forced across the junction against the direction of the Peltier voltage, active heating occurs. When current is forced in the opposite direction, i.e., in the same direction as the Peltier voltage, active cooling occurs. This current can be controlled by thermal control unit TCU (FIG. 4). Temperature regulating element $TRE_1$ can be employed to regulate the entire interior of pump assembly PA so as to regulate other components such as coupling device CD, pump stage 18, plunger 20, and pump interconnect PI. Thermal expansion of any of these components can generate undesirable thermal pumping.

Figure 10A:
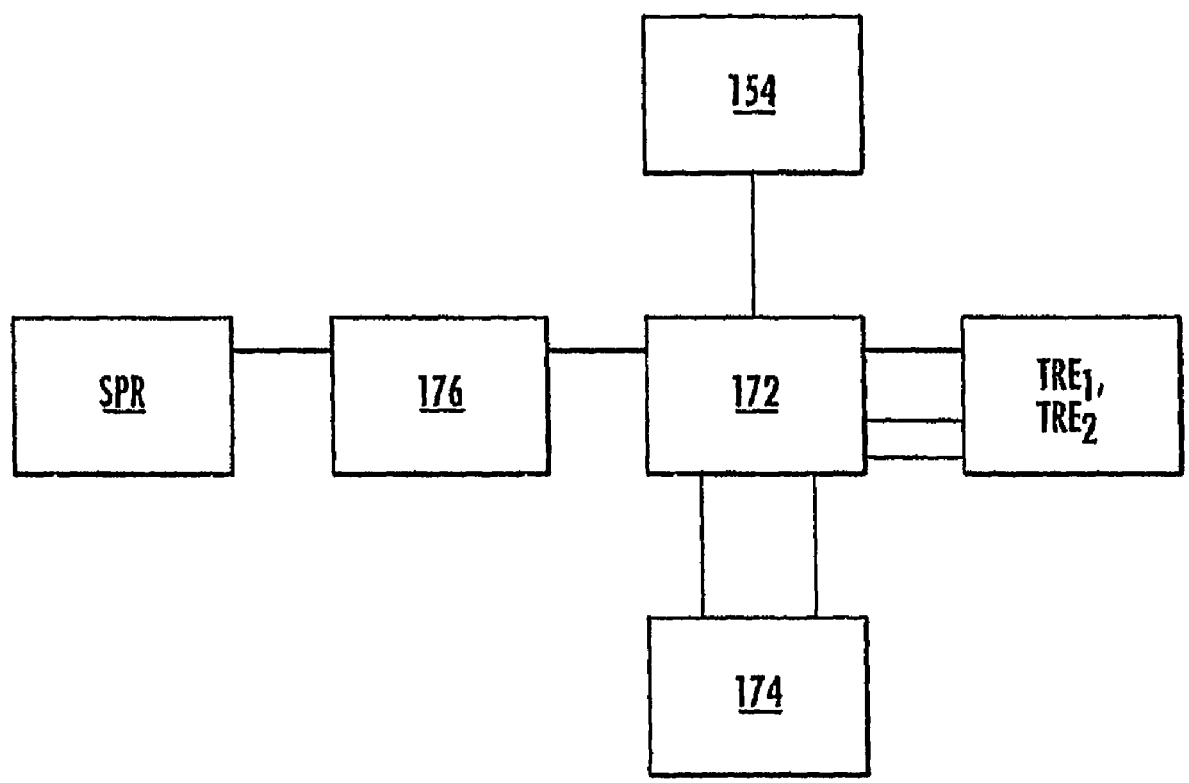
FIG. 10A is a schematic view of temperature regulating circuitry provided in accordance with embodiments disclosed herein.

Referring to FIG. 10A, a general schematic of the temperature control circuitry for implementing temperature regulation of pump assembly PA is illustrated according to an exemplary embodiment. To control the current in temperature regulating element $TRE_1$, the temperature control circuitry can include a proportional-integral-derivative (PID) based thermoelectric module temperature controller 172, such as is commercially available from Oven Industries, Inc., Mechanicsburg, Pa., as Model No. 5C7-361. Temperature controller 172 communicates with a suitable power supply 174 as well as temperature regulating element $TRE_1$, and receives temperature measurement signals from temperature sensing device 154. In addition, temperature controller 172 communicates with signal processing and readout device SPR (see also FIG. 4 and computer $P_C$ in FIG. 5) to provide temperature data thereto and/or receive commands therefrom. If appropriate, temperature controller 172 communicates with signal processing and readout device SPR via a communications module 176 such as an RS-232 to RS-485 converter. Temperature controller 172, power supply 174, and communications module 176 can be integrated as thermal control unit TCU illustrated in FIG. 4. In operation, temperature controller 172 regulates the duty cycle of temperature regulating element $TRE_1$ to maintain a user-selected set point temperature based on the feedback from temperature sensing device 154. According to various embodiments, set point values are either inputted into signal processing and readout device SPR using for example a graphical user interface and sent to temperature controller 172, or directly inputted into temperature controller 172 with user interface hardware (e.g., potentiometers) provided with thermal control unit TCU.

Figure 10B:
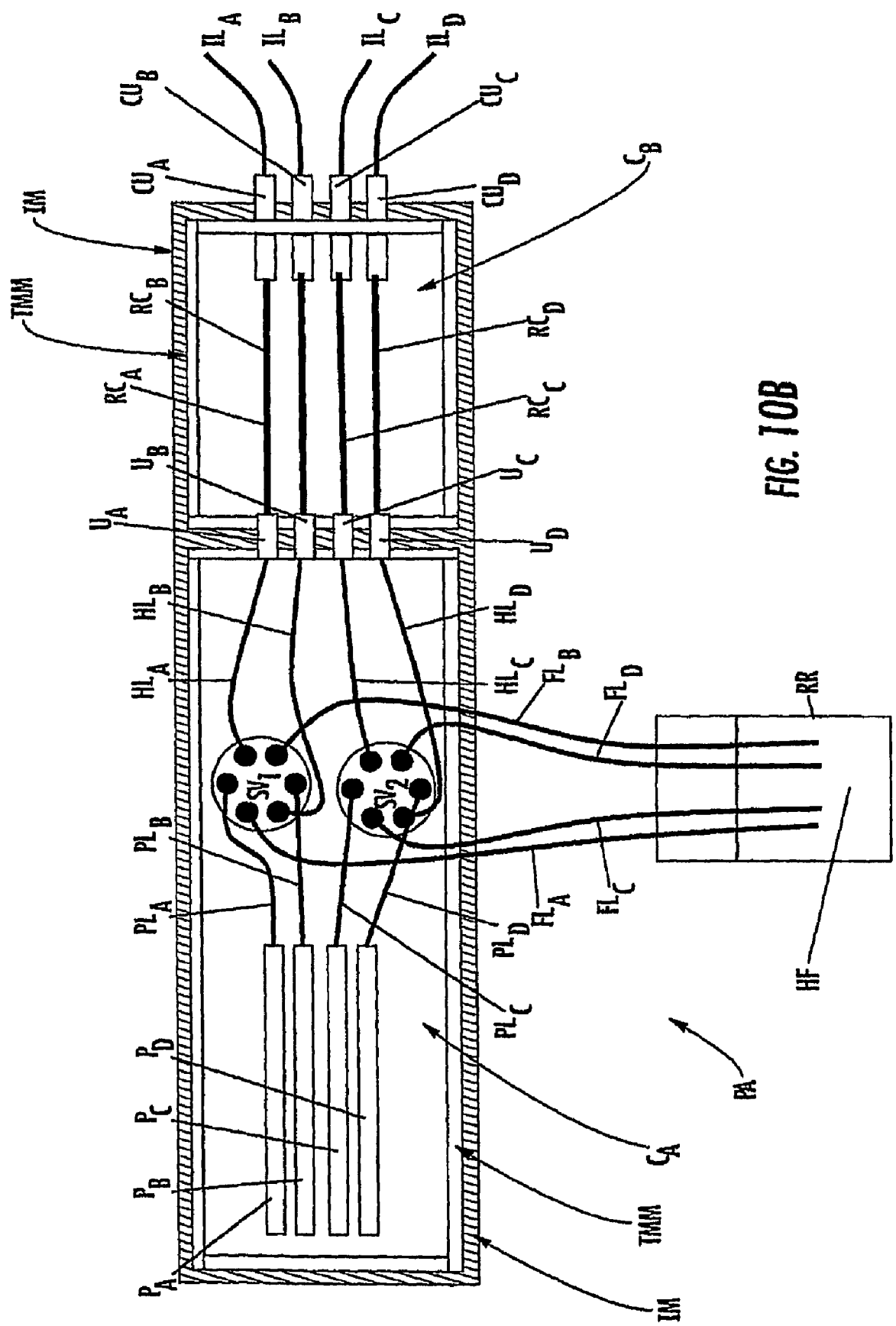
FIG. 10B is a schematic view of a thermally-controlled pump assembly according to embodiments disclosed herein.

FIG. 10B is a schematic view of a thermally-controlled pump assembly, generally designated PA. Two compartments $C_A$ and $C_B$ that house the components of pump assembly PA. Compartments $C_A$ and $C_B$ can be made of thermal mass material TMM comprising the walls, floor, and lid of compartments $C_A$ and $C_B$. Thermal mass material TMM can have large thermal mass, and is typically rigid to provide mechanical integrity to the walls, such as steel, brass, or other metal. Compartments $C_A$ and $C_B$ are insulated with insulating material IM that wraps compartments $C_A$ and $C_B$ and separates compartment $C_A$ from compartment $C_B$. Insulating material IM is a material of low thermal conductivity such as rigid foam. A lid (not shown) made of thermal mass material TMM insulated with insulating material IM encloses compartments $C_A$ and $C_B$. Compartments $C_A$ houses pumps $P_A$-$P_D$ and switching valves $SV_1$ and $SV_2$. Pump lines $PL_A$-$PL_D$ connect, respectively, pumps $P_A$-$P_D$ to switching valves $SV_1$ and $SV_2$. Switching valves $SV_1$ and $SV_2$ thereby switchably connect $PL_A$-$PL_D$ to fill lines $FL_A$-$FL_D$ to or to hydraulic lines $FL_A$-$FL_D$, and pumps $P_A$-$P_D$ can move in reverse to fill with hydraulic fluid HF from refill reservoir RR or switching valves $SV_1$ and $SV_2$ can connect pumps $P_A$-$P_D$ to hydraulic lines $HL_A$-$HL_D$ whereby they pump fluid through unions $U_A$-$U_D$ and into reagent cartridges $RC_A$-$RC_D$, thereby forcing reagent from reagent cartridges $RC_A$-$RC_D$ through chip unions, $CU_A$-$CU_D$ and into a microfluidic chip via interconnect lines (such as interconnect lines $IL_A$-$IL_D$ shown in FIG. 1). This embodiment provides several advantages over the embodiment shown in FIG. 7. Reagent cartridges $RC_A$-$RC_D$ can have a volume greater than pumps $P_A$-$P_D$ to extend the life of a pump before reagents have to be replenished. Pumps $P_A$-$P_D$, having smaller volume, should be refilled periodically with hydraulic fluid HF, which can be achieved through switching valves $SV_1$ and $SV_2$, which permit intermittent connection to refill reservoir RR through fill lines $FL_A$-$FL_D$. Hydraulic fluid HF is a chemically inert fluid that will transmit pressure to the solutions in reagent cartridges $RC_A$-$RC_D$ and on through to the microfluidic chip. Compartment $C_A$ housing the pumps can either be thermally controlled by a thermal regulating element TRE (FIG. 4) as described for FIG. 7 or it can be allowed to remain at ambient. The large thermal mass provided by thermal mass material TMM in concert with thermal isolation provided by insulating material IM can prevent contents of compartment $C_A$ from changing appreciably, reducing thermal pumping. Because pumps $P_A$-$P_D$ are entirely enclosed in compartment $C_A$ then thermal pumping caused by thermal expansion of components, such as plungers 20 (FIG. 2), exposed in the pump in FIG. 7 is reduced. Similarly, the contents of reagent cartridges $RC_A$-$RC_D$ can be thermally regulated by regulating the temperature of compartment $C_B$ via thermal regulating element TRE (FIG. 4) as described for FIG. 7. This permits refrigeration of temperature labile reagents, and the large thermal mass provided by thermal mass material TMM in concert with thermal isolation provided by insulating material IM can hold the contents of compartment $C_B$ at constant temperature, reducing thermal pumping.

Referring back to FIG. 4, in embodiments that include pump temperature regulating device $TRD_1$, and where pump temperature regulating device $TRD_1$ is employed for preserving (i.e., cooling) reagents in pump assembly PA, it will be noted that such reagents can be rapidly brought to reaction temperature upon their introduction into microfluidic chip MFC. This facility can be due at least in part to the small volume of the fluid relative to microfluidic chip MFC and the large surface area to volume ratio of the fluid. Additionally, the reaction temperature can be attained through the use of chip temperature regulating device $TRD_2$, described in detail hereinbelow. The provision of pump temperature regulating device $TRD_1$ eliminates the need for on-chip storage of reagents. The thermal conductance on small microfluidic devices (especially those constructed from glass and silicon) does not easily permit different temperature compartments on one chip. Also eliminated is the need for on-chip heat exchangers, which add cost and complexity to the chip design.

Figure 11A:
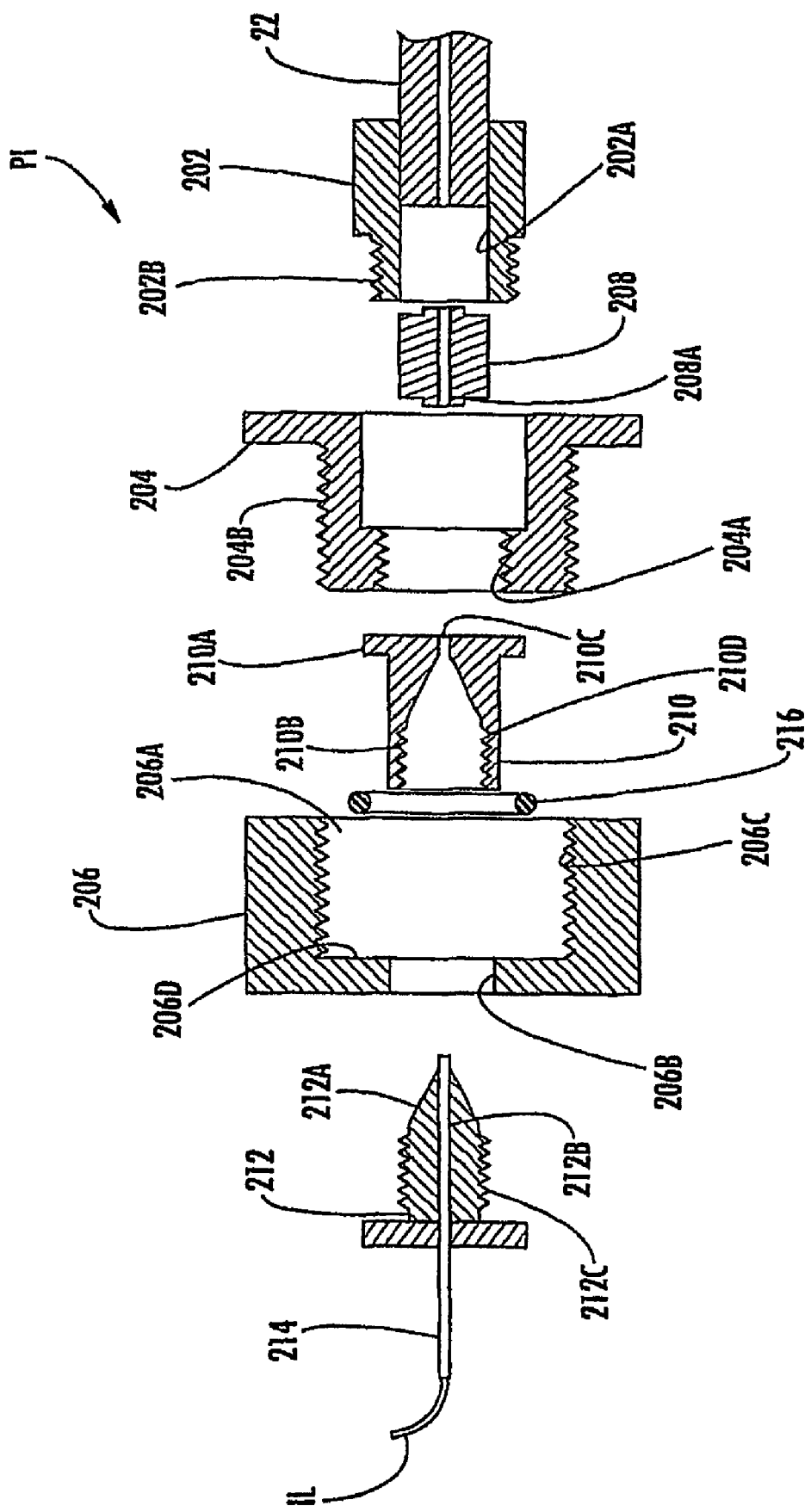
FIGS. 11A and 11B are cross-sectional exploded and assembled views, respectively, of a microfluidic pump interconnect provided in accordance with embodiments disclosed herein.
Figure 11B:
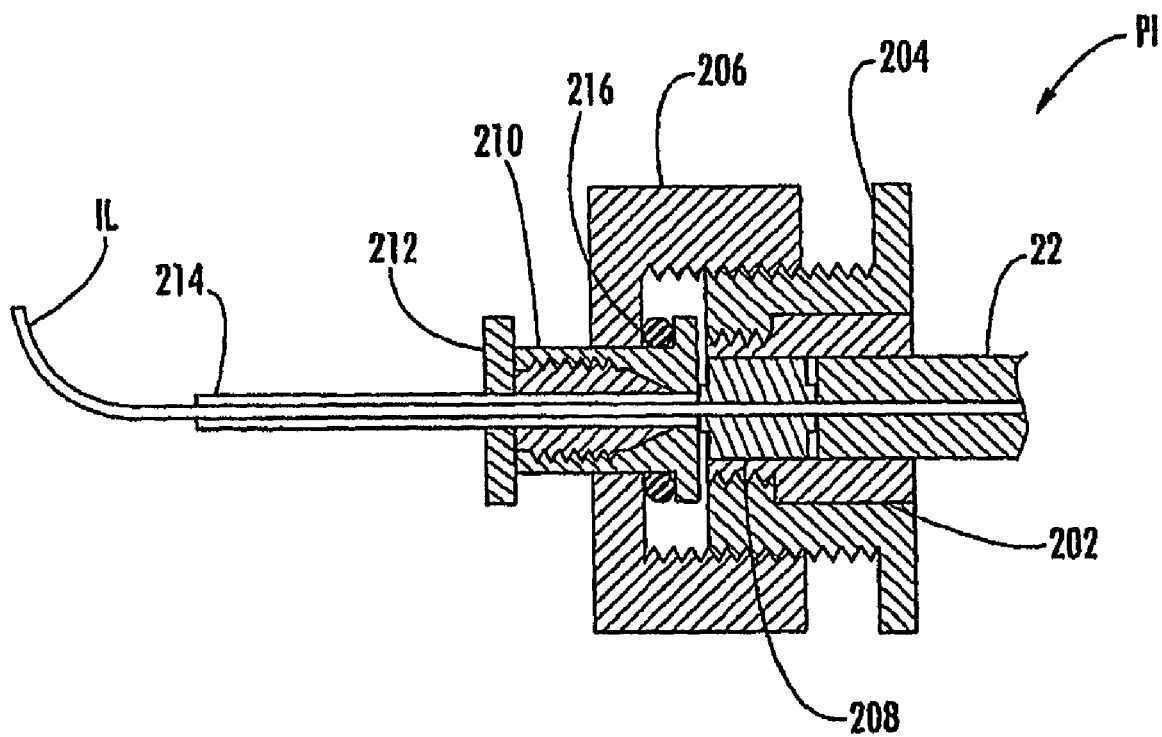

Referring now to the respective exploded and assembly views of FIGS. 11A and 11B, one advantageous embodiment of a pump interconnect, generally designated PI (e.g., pump interconnect $PI_A$, $PI_B$ or $PI_C$ of FIG. 1) is illustrated. Pump interconnect PI can comprise an assembly of colinearly and coaxially interfaced components providing a reliable, fluidly sealed macroscopic-to-microscopic connection with minimal dead volume. In one exemplary embodiment, the dead volume is as low as approximately 70 nl. Moreover, many of the components utilized, particularly those prone to wear or other degradation, are easily removable from the assembly and replaceable. Other components can be bonded to each other by using epoxy adhesive or any other suitable technique.

In the embodiment illustrated in FIGS. 11A and 11B, pump interconnect PI comprises a first annular member 202, a second annular member 204, a third annular member 206, a hollow gasket 208, a female fitting 210, a male fitting 212, and a sleeve 214. These components can be made of any suitable biocompatible, inert material such as stainless steel or various polymers. In some embodiments, female fitting 210, male fitting 212, and sleeve 214 are taken from the NANOPORT™ assembly commercially available from Upchurch Scientific (a division of Scivex), Oak Harbor, Wash. In some embodiments, barrel 22 and first annular member 202 are preassembled pieces belonging to a GASTIGHT microsyringe available from Hamilton Company of Reno, Nev., U.S.A.

First annular member 202 has a bore 202A large enough to receive pump barrel 22. Hollow gasket 208 is sized to effect a fluid seal between pump barrel 22 and female fitting 210 when inserted into bore 202A of first annular member 202. Hollow gasket 208 is inserted far enough to abut the distal end of pump barrel 22, and has a bore 208A fluidly communicating with that of pump barrel 22 and aperture 210C of female fitting 210. In some embodiments, hollow gasket 208 is constructed from polytetrafluoroethylene (PTFE). Second annular member 204 is coaxially disposed about first annular member 202, and is removably secured thereto such as by providing mating threads on an outside surface 202B of first annular member 202 and an inside surface 204A of second annular member 204. Female fitting 210 is disposed within a cavity 206A of third annular member 206 and extends through a bore 206B of third annular member 206. The proximal end of female fitting 210, which can be defined by a flanged portion thereof, abuts the distal end of hollow gasket 208 and may abut the distal ends of first annular member 202 and/or second annular member 204. Female fitting 210 has a bore 210B beginning at a proximal aperture 210C disposed in axial alignment with bore 208A of hollow gasket 208. In the illustrated embodiment, at least a portion of bore 210B of female fitting 210 is tapered, and this tapered profile is complementary to a tapered profile presented by an outside surface 212A of male fitting 212 to effect a removable seal interface.

Third annular member 206 is coaxially disposed about second annular member 204, and is removably secured thereto such as by providing mating threads on an outside surface 204B of second annular member 204 and an inside surface 206C of third annular member 206. This feature enables third annular member 206 to be axially adjustable relative to second annular member 204 so as to bias hollow gasket 208 toward pump barrel 22, thereby improving the sealing interface of hollow gasket 208 between female fitting 210 and pump barrel 22. A sealing member 216, such as an annular gasket or o-ring, can be disposed in cavity 206A of third annular member 206 and is compressed between flanged portion of female fitting 210 and an inside surface 206D of cavity 206A, thereby improving the seal between the inside space of pump interconnect PI and the ambient environment by ensuring that the assembly of female fitting 210 and male fitting 212 sits flat against hollow gasket 208.

Male fitting 212 is inserted into bore 210B of female fitting 210, and has a bore 212B that is axially aligned with proximal aperture 210C of female fitting 210. In some embodiments, male fitting 212 is removably secured to female fitting 210 by providing mating threads on an outside surface 212C of male fitting 212 and an inside surface 210D of bore 210B of female fitting 210. Input line IL, provided for connection with microfluidic chip MFC as described hereinabove with reference to FIG. 1, is inserted through bore 212B of male fitting 212 to extend through proximal aperture 210C in fluid communication with bore 208A of hollow gasket 208. In some embodiments, a sleeve 214 is inserted through bore 212B of male fitting 212 coaxially around input line IL.

Figure 11C:
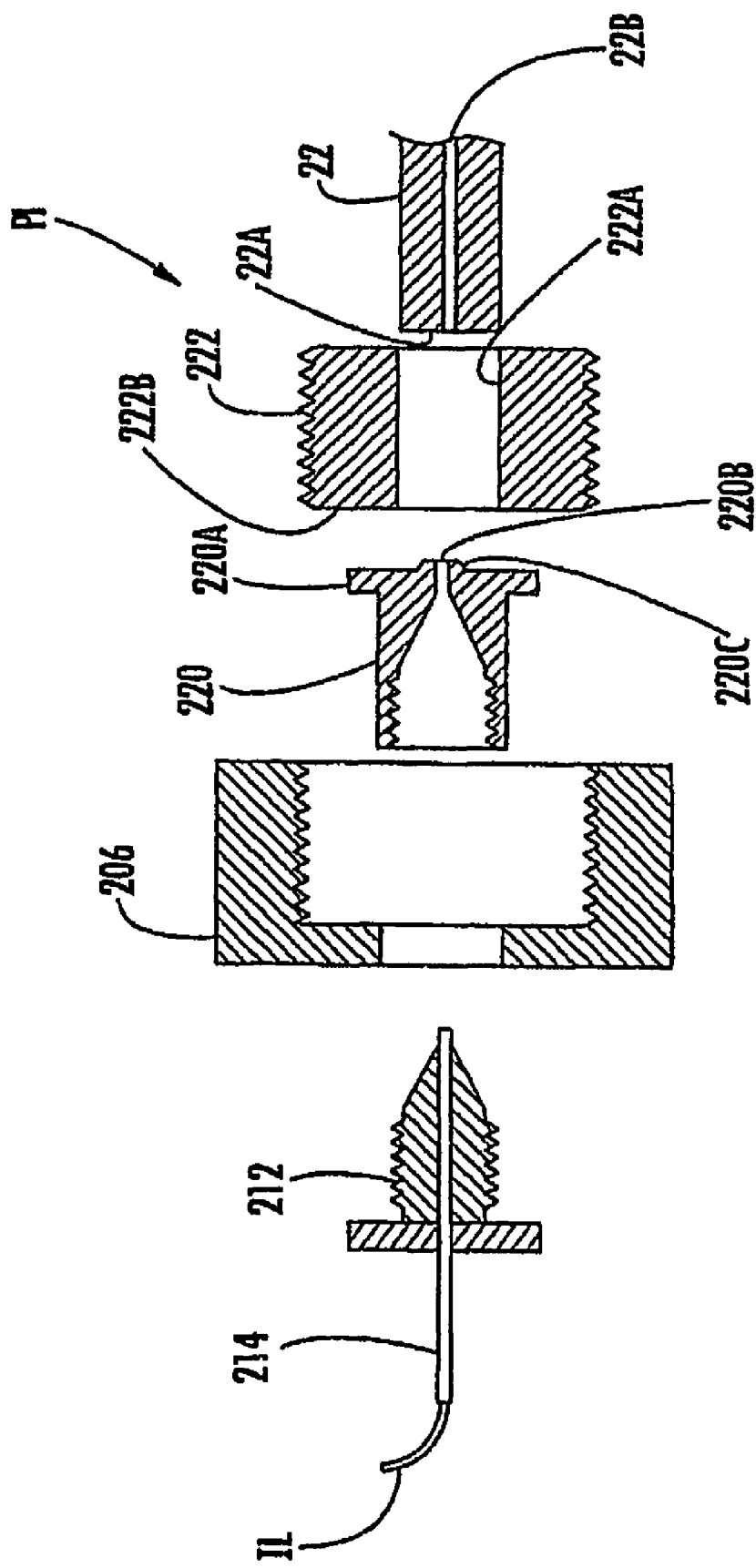
FIG. 11C is a cross-sectional exploded view of a microfluidic pump interconnect provided in accordance with embodiments disclosed herein.

FIG. 11C is a cross-sectional exploded view of a microfluidic pump interconnect, generally designated PI. Pump interconnect PI comprises a first annular member 222, a second annular member 206, a female fitting 220, a male fitting 212, and a sleeve 214. According to one embodiment, female fitting 220, male fitting 212, and sleeve 214 are components of the NANOPORT™ available from Upchurch Scientific. In addition, according to one embodiment, barrel 22 is a GASTIGHT® microsyringe available from Hamilton Company. Female fitting 220 can be identical to female fitting 210 shown in FIG. 11A, however, the side of female fitting 220 containing aperture 220B may be machined back to produce a nipple 220C that directly seals against the glass surface of barrel 22.

Referring to FIG. 11C, annular member 222 has a bore 222A large enough to receive pump barrel 22, and these two parts are glued together with epoxy such that a front face 22A of barrel 22 extends slightly beyond front face 222B of first annular member 222. Second annular member 206 is then screwed onto first annular member 222 engaging flanges 220A of female fitting 222 and forcing nipple 220C against the front face 22A of barrel 22 such that aperture 220B is in fluid communication with barrel bore 22B, and nipple 220C forms a pressure tight seal against front face 22A of barrel 22.

Figure 12A:
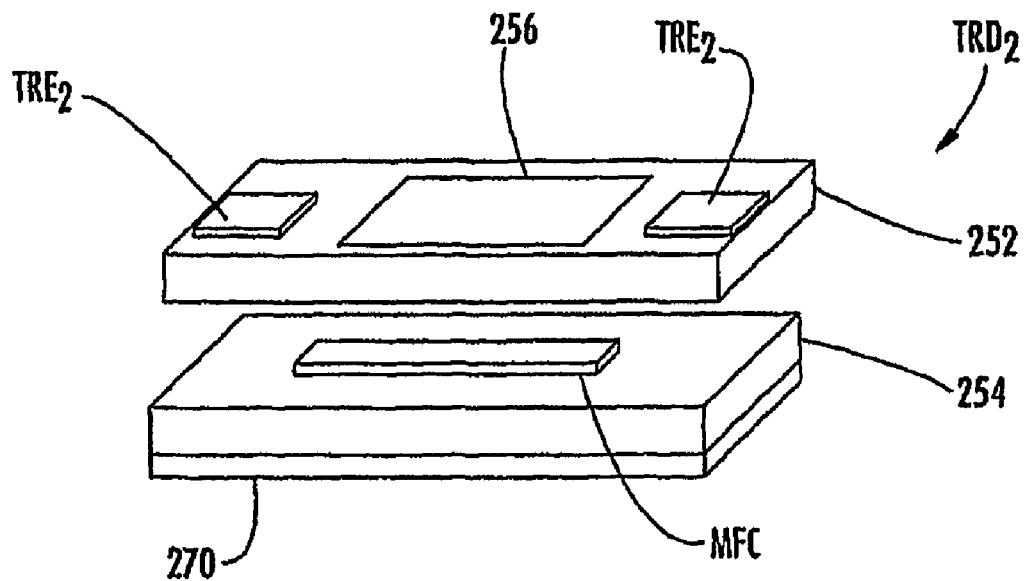
FIGS. 12A and 12B are perspective unassembled and assembled views, respectively, of a microfluidic chip encapsulated within a temperature regulating device in accordance with embodiments disclosed herein.
Figure 12B:
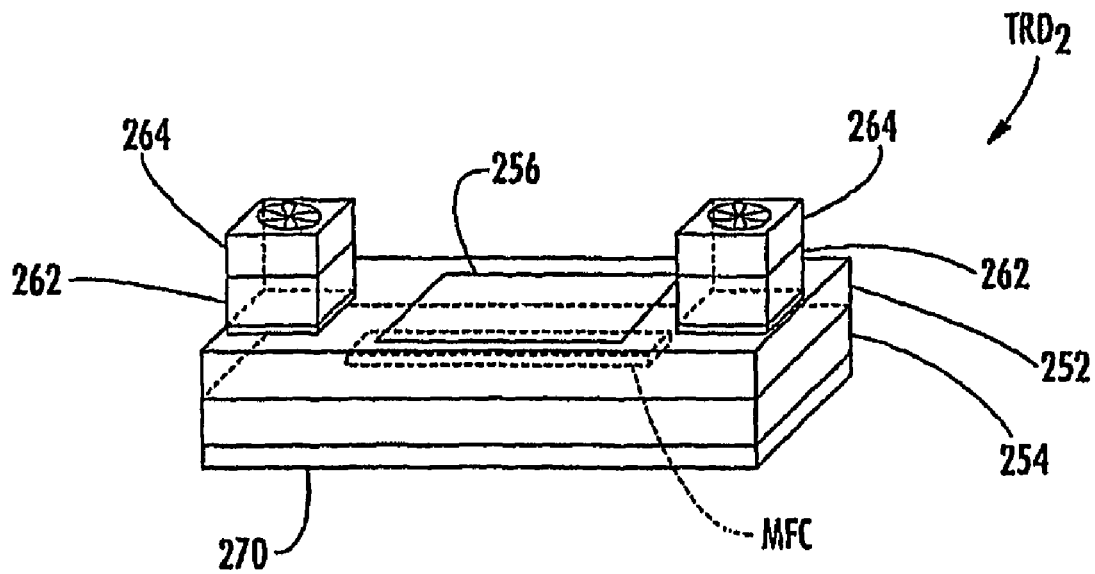

Referring now to FIGS. 12A and 12B, an advantageous embodiment of chip temperature regulating device $TRD_2$ is illustrated. Microfluidic chip MFC can be encapsulated within chip temperature regulating device $TRD_2$ to thermally isolate microfluidic chip MFC from ambient temperature fluctuations, stabilize fluid flow, control the temperature of a biochemical reaction proceeding in or on microfluidic chip MFC, and/or stabilize the position of microfluidic chip MFC and its alignment with other components such as excitation source ES (FIGS. 4 and 5) by minimizing thermally induced motions of one or more components of microfluidic chip MFC, any or all of which can contribute to reducing thermal noise and consequently improving the quality of measurement data acquired during concentration gradient runs. In one specific embodiment, chip temperature regulating device $TRD_2$ can control chip temperature within a range of approximately 4° C. to 70° C. to within 0.1° C. of accuracy. Thus, the temperature of microfluidic chip MFC, and/or one component thereof or associated therewith, and/or the liquid processed by microfluidic chip MFC, can be controlled.

Figure 13:
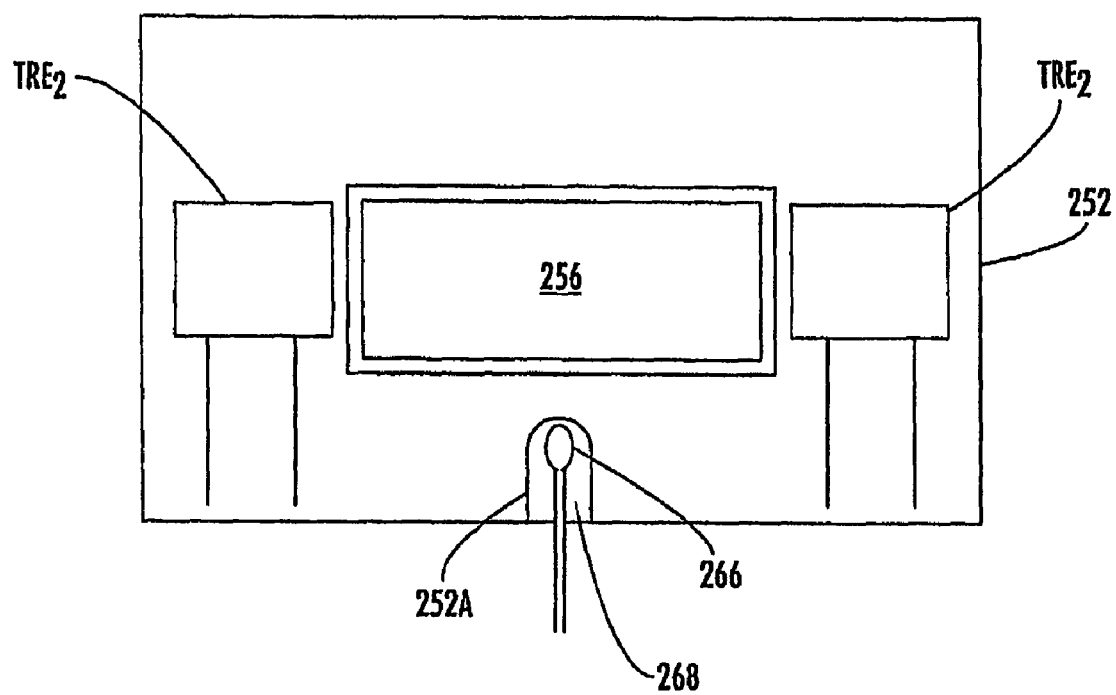
FIG. 13 is a top plan view of an upper portion of the temperature regulating device illustrated in FIGS. 12A and 12B.
Figure 14:
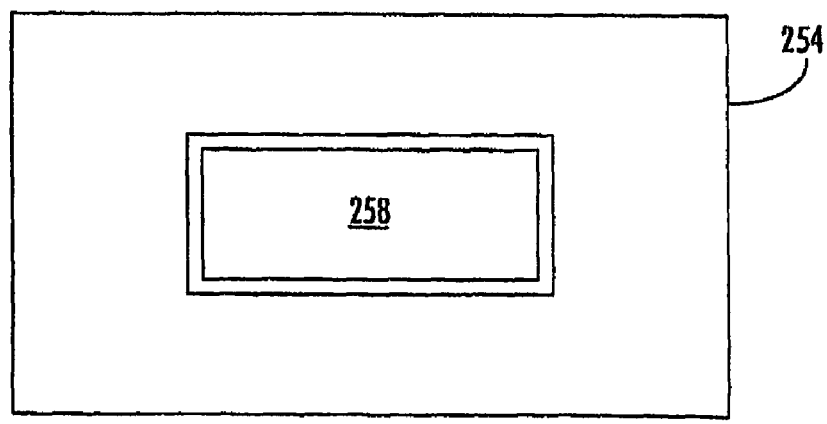
FIG. 14 is a bottom plan view of a lower portion of the temperature regulating device illustrated in FIGS. 12A and 12B.

As illustrated in FIGS. 12A and 12B, microfluidic chip MFC can be encapsulated between a first thermally conductive body or top plate 252 and a second thermally conductive body or bottom plate 254. First and second bodies 252 and 254 can be constructed from any suitably efficient thermally conductive material, one non-limiting example being aluminum, and bonded together by any suitable means. As illustrated in FIGS. 13 and 14, first and second bodies 252 and 254, if constructed from a light-scattering and/or an insufficiently light-transmissive material, can each include an optically clear window 256 and 258, respectively, to enable microfluidic chip MFC to be optically interrogated from either the top or the bottom. In one exemplary embodiment, first and second bodies 252 and 254 are each approximately 0.25 inch thick and have a planar area of approximately 3×5 inches, with their respective windows 256 and 258 having an area of approximately 25×50 mm.

Referring specifically to FIG. 13, one or more temperature regulating elements $TRE_2$ are attached to first thermally conductive body 252 by any suitable means to provide active heating and/or cooling. In advantageous embodiments, each temperature regulating element $TRE_2$ is a thermoelectric device such as a Peltier device, which is described hereinabove and illustrated in FIG. 9. To remove heat generated by temperature regulating elements $TRE_2$ during operation, a heat sink 262 can be attached to each temperature regulating element $TRE_2$ as shown in FIG. 12B. Additional cooling means can be provided for cooling heat sink 262 if desired, such as cooling fans 264 shown in FIG. 12B or by circulating a suitable heat transfer medium such as water through heat sinks 262. As shown in FIG. 13, a suitable temperature measuring or sensing device 266 such as a thermistor is embedded or otherwise placed in thermal contact with first body 252 (or, alternatively, second body 254) to provide real-time temperature feedback for thermal control unit TCU (FIG. 4). In the example illustrated in FIG. 13, temperature sensing device 266 is inserted into a cavity 252A formed in first body 252 and secured using a thermally conductive epoxy 268. Alternatively, temperature sensing device 266 can be embedded in, or otherwise placed in thermal contact with, microfluidic chip MFC itself. As a further alternative, temperature sensing device 266 thus built into microfluidic chip MFC can be in contact with the liquid residing or flowing in one or more of the channels of microfluidic chip MFC.

In other advantageous embodiments, if cooling of microfluidic chip MFC is not necessary, temperature regulating element or elements $TRE_2$ comprise resistive heating elements, which are readily commercially available and appreciated by persons skilled in the art. These can eliminate the need for heat sinks 262 and cooling fans 264. In one specific exemplary embodiment, shown in FIG. 14, the resistive heating element can be provided in the form of a transparent, conductive coating that is applied to first body 252 (not shown) and/or second body 254 or portions thereof. In a more specific example, the transparent, conductive coating is composed of a metal oxide such as indium oxide, tin oxide, or indium tin oxide (ITO). Particularly when the resistive heating element is based on a metal oxide, first body 252 and second body 254 can be constructed from a glass-based material, or the metal oxide can be on windows 256 and 258. This has the added advantage of providing a uniform heating source across the plane of microfluidic chip MFC, eliminating thermal gradients from the center of windows 256 and 258 to the edge of the window which are difficult to avoid if heating is from the edge of windows 256 and 258 and especially if windows 256 and 258 should be thin to accommodate optical access.

Second thermally conductive body 254 can serve passively as a large thermal mass to limit temperature fluctuations and isolate microfluidic chip MFC from ambient air currents. The lower periphery of second body 254 can include an insulating layer 270 to thermally isolate second body 254 from any chip holder CH (FIG. 4) such as microscope stage ST (FIG. 5) to which the encapsulated microfluidic chip MFC is to be mounted.

First body 252 is attached directly to second body 254 by any suitable means. Accordingly, thermal management of microfluidic chip MFC can be accomplished by operating temperature regulating devices to create temperature gradients directed either from first body 252 toward second body 254 (i.e., heating) or from second body 254 toward first body 252 (i.e., cooling), but should permit sufficient thermal contact between first body 252 and second body 254 to permit rapid dissipation of thermal gradients between the two, creating a nearly homogenous thermal environment for microfluidic chip MFC. The operation of chip temperature regulating device $TRD_2$ can be controlled as described hereinabove regarding pump temperature regulating device $TRD_1$, using the temperature control circuitry illustrated in FIG. 10A.

An alternate embodiment of the temperature regulating device $TRD_2$ includes only a heat-producing device, comprising, for example, one or more heating elements mounted directly to or otherwise in thermal contact with microfluidic chip MFC, that is used to heat microfluidic chip MFC above ambient temperature. This permits microfluidic chip MFC to operate at the physiological range of many enzymes (e.g. 37° C.) and also accelerates the rate of enzyme action. In this embodiment, the ambient environment removes heat from the temperature regulating device $TRD_2$ obviating any need for specialized heat dissipating components.

Connection of external pumps $P_A$-$P_D$ to microfluidic chip MFC and to external components, such as switching valves and plate handlers as discussed below, requires the use of tubes or other conduits. These should be of minimal internal volume for efficient use of reagents, and their walls should have minimal compliance to avoid their behaving like a pressure "capacitor" in which the walls expand (and thus the internal volume increases) as pressure increases to drive fluid flows. Materials such as fused silica can be readily obtained as microcapillaries with small internal diameters and rigid walls. Additionally, the capillaries should be shielded from thermal fluctuations because thermal expansion of the capillaries will cause them to behave like thermal pumps, and oscillations in temperature will result in noise in the flows through these capillaries. Such shielding can be either as an insulative wrap around the capillaries, or all components of the system, including the capillaries, can be housed in a single temperature-controlled enclosure.

Figure 15A:
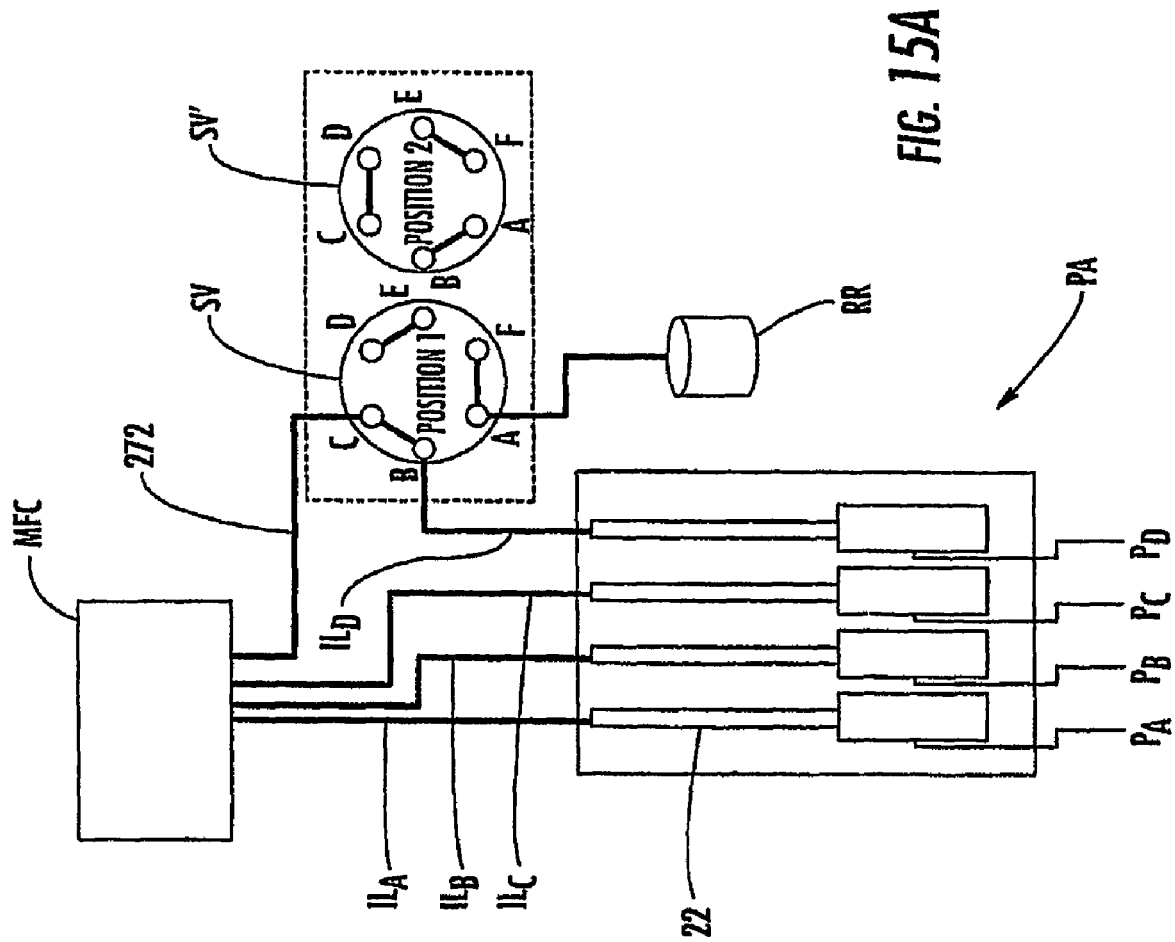
FIGS. 15A, 15B and 15C are respective schematic diagrams of examples of three alternative liquid handling systems that can be integrated with the embodiments of the sample processing apparatus disclosed herein.
Figure 15B:
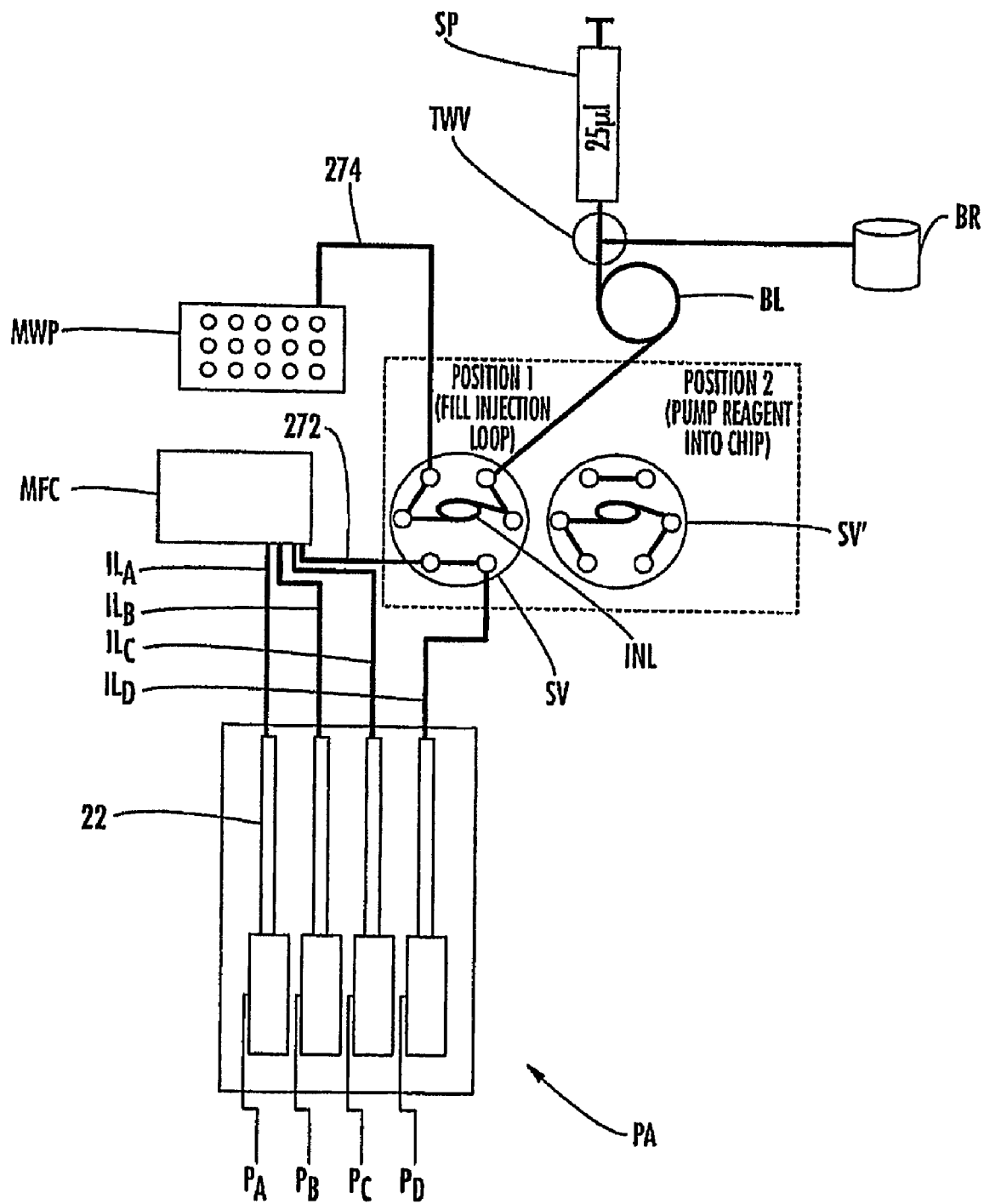
Figure 15C:
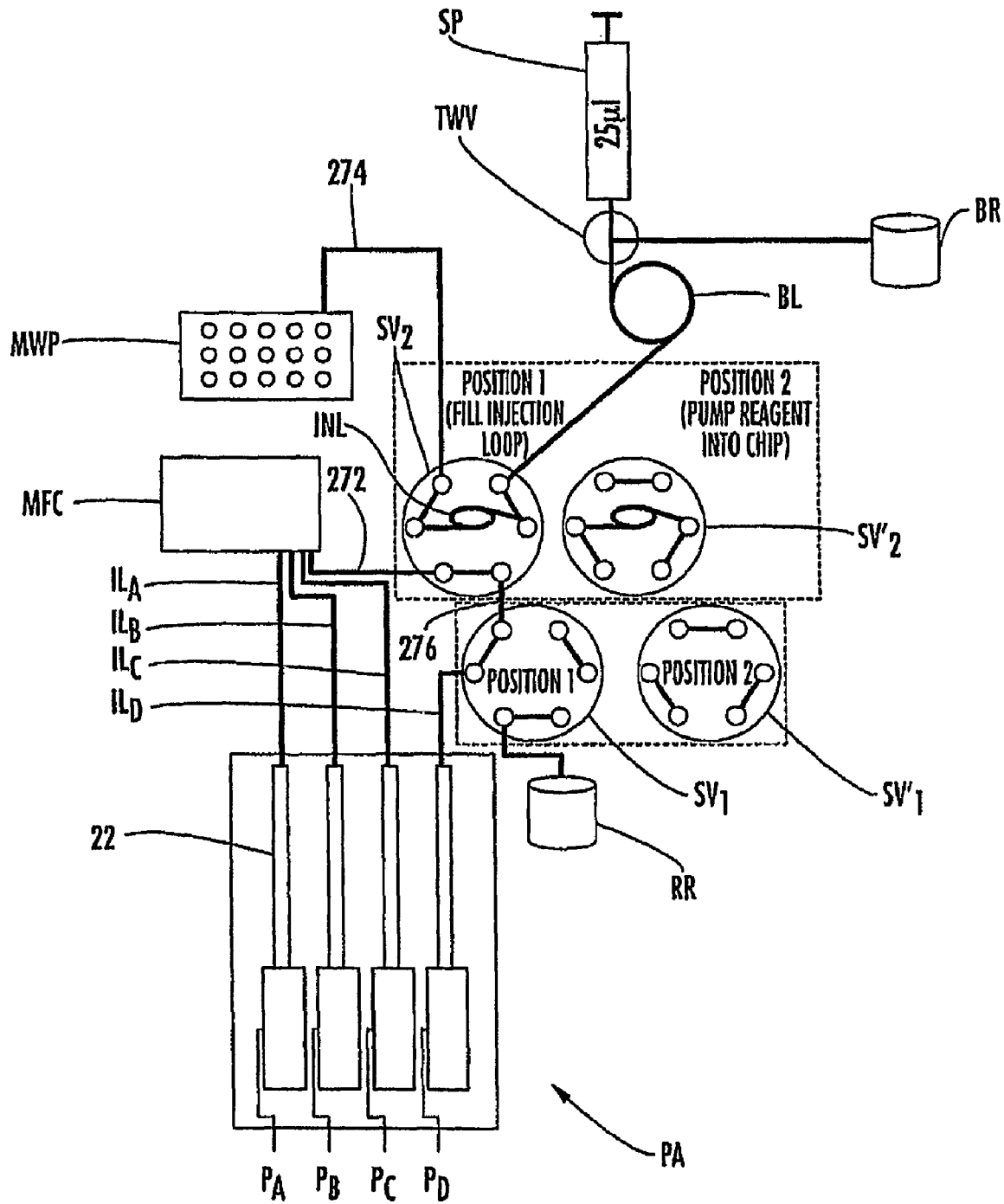

Referring now to FIGS. 15A-15C, non-limiting examples of liquid handling systems are illustrated. These systems can be implemented with pump assembly PA in accordance with any of the embodiments of sample processing apparatus SPA disclosed herein. The automation provided by these systems offers many advantages. First, the automation can allow unattended refill of reagents in pumps $P_A$-$P_D$, thus enabling the system to run unattended without operator intervention for days at a time. Second, the automation can allow automatic change of reagent in pumps $P_A$-$P_D$, and thus allow the system to test a series of reagents such as in screening pharmaceutical compounds, as well as the automatic reconfiguration of loaded reagents to automatically test the network of hypotheses for automated assay development and automatic hypothesis testing with intelligent systems. The automation also reduces the frequency that operators need to make and break fluidic interconnects. Thus, contamination and air bubbles in the system can be reduced, and the service life of the fluidic interconnects extended. These systems can incorporate an automated liquid handler that can be computer controlled via integrated computer software as part of any embodiment of the microfluidic systems disclosed herein. Managing the microfluidic system with a single software package enables real time decision-making and feedback control, thereby giving the system unprecedented flexibility and run time. This approach has not heretofore been practicable for displacement flows, because of the absence of displacement pumps that pump slowly enough for microfluidic systems as discussed hereinabove. An example of a suitable automated liquid handling system is the FAMOS™ micro autosampler available from LC Packings, Sunnyvale, Calif. This system provides for automated sample injection of any volume ranging from 50 nl up to 25/µl from 96- and 384-well plates. The device can include a sample tray that is equipped with Peltier cooling to avoid degradation of thermally labile samples.

Referring to FIG. 15A, addition of reagent to one or more of pumps $P_A$-$P_D$ can be achieved through inclusion of a switching valve SV located between one or more pumps $P_A$-$P_D$ and an external reagent reservoir RR (connection to pump $P_A$ is shown in FIG. 15A). An example of a suitable switching valve SV is a multi-port valve having a number of ports A-F available through which fluid can be selectively conducted. As appreciated by persons skilled in the art, a multi-port valve typically has a rotatable internal body containing internal passages. Through actuation of the internal body, either manually or via programmable control, each internal passage can be aligned with a pair of ports in order to selectively define one or more fluid flow paths through the valve. Switching valve SV can switch such that its associated pump $P_A$, $P_B$, $P_C$ or $P_D$ communicates alternately between microfluidic chip MFC (the first position schematically illustrated in FIG. 15A, where the switching valve is designated SV) and external reagent reservoir RR (the second position in FIG. 15A, where the switching valve is designated SV'). Pumps like syringe pumps contain a finite reservoir (e.g. the barrel of a gastight syringe may only contain 10 µl). When used in pumps $P_A$-$P_D$, the pumps can run out of reagent, and switching valve SV can switch such that the pump is in communication with external reagent reservoir RR, and then the pump can work in reverse, pumping reagent back into barrel 22 of the pump whereby the pump is reloaded with reagent. This permits extended runs of the system without human intervention. Refrigeration of external reagent reservoir RR permits extended storage of temperature-labile reagents.

Referring to FIG. 15B, switching valve SV can also be used in combination with one or more of pumps $P_A$-$P_D$ and an automated plate handler to perform automated addition of reagent or wash buffers from a multi-well plate MWP (e.g. a 96-well or 384-well plate). According to one embodiment, switching valve SV can be equipped with an injection loop having a volume of 1.0 microliter. Switching valve SV can include injection loop INL having fused silica lined PEEK® tubing. Multi-well plate MWP can be refrigerated to preserve temperature-labile reagents. This configuration enables serial addition of different reagents, for example, to screen inhibitors against an enzyme or to test multiple reagents for optimization of a biochemical reaction, or to provide wash buffers or rinsing fluids.

In this embodiment, switching valve SV again has two positions (SV and SV') and 6 or another number of ports as needed. Switching valve SV can permit the addition of only small amounts of reagent (sub-microliter) into a capillary 272 in between a pump $P_A$, $P_B$, $P_C$ or $P_D$ and microfluidic chip MFC, obviating the need to flush the pump $P_A$, $P_B$, $P_C$ or $P_D$ in between reagent changes. Reagents from multi-well plate MWP can be aspirated into a capillary 274 connected to switching valve SV. As appreciated by persons skilled in the art of automated liquid handling, the tip of capillary 274 can be carried on a motorized, programmable X-Y or X-Y-Z carriage or other robotic-type effector, permitting removal of reagent from any well in multi-well plate MWP. This capillary tip can be fitted with an independently actuated needle for piercing foil, plastic film or other types of septa used to seal the wells of multi-well plate MWP. Multi-well plate MWP can include 96 wells or another suitable number of wells. When injection loop INL is to be filled, the capillary 274 can be lowered into a well containing the fluid to be injected.

As shown in FIG. 15B, a syringe pump SP can be employed to implement the movement of reagents. Syringe pump SP can be provided as part of a suitable, commercially available automated liquid handling system as noted hereinabove. Syringe pump SP can be a larger liquid movement instrument (e.g., 25 µl) in comparison with pumps $P_A$-$P_D$, with coarser control and more rapid flow rates, thereby permitting rapid change of reagents and flushing of reagents from injection loop INL. Syringe pump SP can pull reagent from a selected well of multi-well plate MWP and into injection loop INL. Before stopping, syringe pump SP can pull sufficient volume from the selected well to fill capillary 274, injection loop INL, and excess to further flush injection loop INL with the fluid. While injection loop INL is being filled in position 1, one of pumps $P_A$, $P_B$, $P_C$ and $P_D$ can be used to push solvent through capillaries $I_A$, $I_B$, $I_C$ and $I_D$, respectively, for flushing capillaries $I_A$, $I_B$, $I_C$ and $I_D$ and microfluidic chip MFC. When switching valve SV is switched back to position SV' in position 2, injection loop INL becomes placed in line with pump $P_A$ allowing pump $P_A$ to push the fluid in injection loop INL into microfluidic chip MFC.

When switching valve SV switches to position 2, one of pumps $P_A$, $P_B$, $P_C$ and $P_D$ can be connected through injection loop INL to microfluidic chip MFC. One of pumps $P_A$, $P_B$, $P_C$ and $P_D$ can advance fluid from injection loop INL through a corresponding capillary $I_A$, $I_B$, $I_C$ and $I_D$ into microfluidic chip MFC. Simultaneously, the carriage can move capillary 274 to a well of multi-well plate MWP having a rinsing fluid. Syringe pump SP can then repeatedly pull fluid into and then expel fluid from capillary 274 to rinse it clean.

Furthermore, syringe pump SP can be placed in communication with a three-way valve TWV, an external buffer reservoir BR, and a buffer loop BL (if additional buffer volume is needed or desired) to enable syringe pump SP to flush injection loop INL with buffer. Three-way valve TWV can permit refilling of syringe pump SP from buffer reservoir BR, preventing contamination of syringe pump SP and associated lines with any fluid from injection loop INL and the alternate fluid connection with buffer loop BL.

Referring to FIG. 15B, when it is time to advance the next fluid in sequence into microfluidic chip MFC, one of pumps $P_A$, $P_B$, $P_C$ and $P_D$ can stop and switching valve SV can move to position 1. Syringe pump SP can then pull rinsing fluid through injection loop INL to flush it clean or it can push fluid from buffer reservoir BR to flush injection loop INL clean. Next, capillary 274 can be moved to the next well of multi-well plate MWP and the process repeated.

Referring to FIG. 15C, multiple combinations of switching valves and three-way valves can also be used in combination with one or more of pumps $P_A$-$P_D$ and an automated plate handler to realize more complex schemes, such as to permit addition of multiple reagents and refill of the buffer used as a hydraulic fluid in syringe pump that pumps through injection loop. For instance, one or more pairs of multi-port switching valves $SV_1$ and $SV_2$ can be interposed in the liquid circuit between microfluidic chip MFC and one or more corresponding pumps $P_A$-$P_D$. One of the ports of first switching valve SV$_1$ communicates with external reagent reservoir RR, and another of its ports communicates with pump P$_A$, P$_B$, P$_C$ or P$_D$ and its input line IL$_A$, IL$_B$, IL$_C$ or IL$_D$, and another port communicates with a port of second switching valve SV$_2$ via a transfer line 276. Another port of second switching valve SV$_2$ communicates with microfluidic chip MFC, thus providing fluidic communication with pump P$_A$, P$_B$, P$_C$ or P$_D$ and microfluidic chip MFC. Other ports of second switching valve SV$_2$ communicate with capillary 272 and buffer loop BL, respectively. Injection loop INL is connected to second switching valve SV$_2$.

In the present, exemplary configuration, first switching valve SV$_1$ has two primary positions (the first position designated SV$_1$ and the second position designated SV'$_1$) and second switching valve SV$_2$ likewise has two primary positions (the first position designated SV$_2$ and the second position designated SV'$_2$). When both switching valves SV$_1$ and SV$_2$ are in their respective first positions, their corresponding pump of pump assembly (pump P$_D$ in the illustrated embodiment) fluidly communicates with an input of microfluidic chip MFC. At its second position, first switching valve SV'$_1$ permits pump P$_D$ to draw additional reagent from reagent reservoir RR for refilling purposes. At its first position, second switching valve SV$_2$ can fill injection loop INL with a reagent selected from multi-well plate MWP, or flush injection loop INL with buffer from the system comprising syringe pump SP, three-way valve TWV, external buffer reservoir BR, and buffer loop BL, as described hereinabove. At its second position, second switching valve SV'$_2$ brings injection loop INL into fluid communication between pump assembly PA and microfluidic chip MFC, allowing the selected reagent residing in injection loop INL to be supplied to microfluidic chip MFC under the fine, precise control of the associated pump of pump assembly PA (pump P$_D$ in the illustration).

As described hereinabove, each component of the systems illustrated in FIGS. 15A-15C can be individually thermally insulated, or the entire system can be disposed in a thermally insulated or regulated enclosure.

Adsorption of a molecule to the wall of a microfluidic channel can sometimes present a problem in microfluidic and other miniaturized systems in which the ratio of surface area to volume is many orders of magnitude larger than is found in more conventional approaches, such as for example, dispensing and mixing of solutions in microtiter plates. Adsorption of molecules in microfluidic systems and other miniaturized devices can be a major obstacle to miniaturization as the adsorption can affect molecule concentrations within fluids, thereby negatively impacting data collected from the microfluidic systems or other miniaturized devices. Adsorption driven changes in concentration can be especially problematic for microfluidic systems used to generate concentration gradients.

In some embodiments, the presently disclosed subject matter provides apparatuses and methods for using the same that can decrease the interference of adsorption to concentration dependent measurements, such as in biochemistry reactions including IC$_{50}$ determinations, by altering the geometry of a microfluidic channel. Although adsorption may not be eliminated, the change in concentration caused by adsorption can be minimized. In general terms, the effects of adsorption on measurements can be minimized by reducing the ratio of channel surface area to fluid volume within the channel (S/V), which also increases diffusion distances. However, as a high surface area to volume ratio can be an unavoidable consequence of the miniaturization of microfluidics, the geometries provided by some embodiments of the presently disclosed subject matter to minimize adsorption consequences are most unexpected by persons in the field of microfluidics. The presently disclosed subject matter provides for, in some embodiments, using large channel diameters in regions of the microfluidic chip most affected by adsorption of reaction components, that is, in regions where a reaction proceeds and/or where measurements are taken. In some embodiments of the presently disclosed subject matter, and with reference to the microfluidic chip embodiment shown in FIG. 1, large channel diameters at detection point DP can be provided to reduce adsorption effects, as a substitute for or in combination with aging loop AL (also referred to as a serpentine analysis channel).

Figure 16:
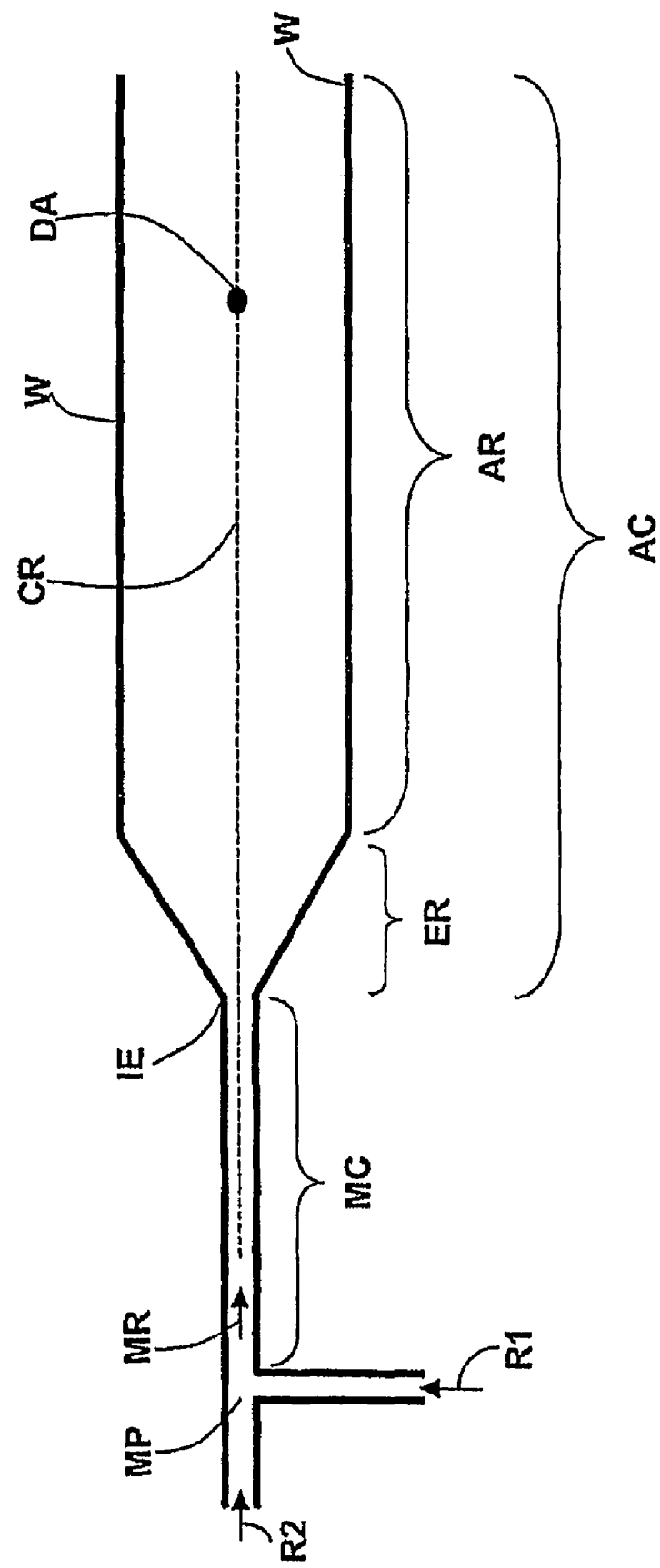
FIG. 16 is a schematic top view of an embodiment of an analysis channel disclosed herein and upstream fluidly communicating microscale channels.

Turning now to FIG. 16, an embodiment of a novel analysis channel of the presently disclosed subject matter is illustrated in a top view. FIG. 16 shows the direction of flow by arrows R1 and R2 of two fluid reagent streams, which can combine at a merge region or mixing point MP. After combining into a merged fluid stream, the reagents within the stream can flow in a direction indicated by arrow MR down a mixing channel MC that can be narrow to permit rapid diffusional mixing of the reagent streams, thereby creating a merged fluid reagent stream. The fluid stream of reagents can then pass into an analysis channel AC, at an inlet or inlet end IE that can have a channel diameter and a cross-sectional area equivalent to that of mixing channel MC. The merged fluid stream can then flow through an expansion region ER that can have a cross-sectional area that can gradually increase and where the surface area to volume ratio can thereby gradually decrease. The merged fluid stream can then continue into an analysis region AR of analysis channel AC with an enlarged cross-sectional area and a reduced surface area to volume ratio. A reaction can be initiated by mixing of the reagent streams at the mixing point MP. However, due to continuity of flow, the flow velocity slows dramatically in analysis region AR of analysis channel AC, and the majority of transit time between mixing point MP and a detection area DA is spent in the larger diameter analysis region AR. Measurements can be made inside this channel, such as with confocal optics, to achieve measurements at detection area DA, which can be located at a center axis CR of analysis region AR of analysis channel AC. Center analysis region CR can be a region equidistant from any channel wall W of analysis channel AC. Thus, the fluid at center analysis region CR of detection area DA can be effectively "insulated" from adsorption at channel walls W. That is, the amount of any reagents removed at channel wall W can be too small, due to the greatly decreased surface area, and the diffusion distance to channel wall W can be too long, due to the greatly increased diffusion distance from center analysis region CR to channel wall W, to greatly affect the concentration at centerline CL. The confocal optics, for example, can reject signal from nearer channel wall W of analysis region AR, permitting measurements to be made at center analysis region CR where the concentration is least affected by adsorption at channel wall W.

A consequence of increasing analysis channel AC cross-section by increasing channel diameter is that the ratio of channel surface area to fluid volume (S/V) within the channel is decreased, relative to a narrower channel. For example, to measure a reaction 3 minutes after mixing, with a volumetric flow rate of 30 nL/min, the reaction should be measured at a point in the channel such that a microfluidic channel section spanning from mixing point MP to detection area DA encloses 90 nL. For an analysis channel with a square cross-section and a diameter of 25 µm, this point is about 144 mm downstream from mix point MP. This channel has a surface area of $1.44 \times 10^{-5}$ square meters, yielding a surface to volume ratio S/V equal to $1.6 \times 10^{-5}$ m$^{-1}$. For a channel with a diameter of 250 µm, the measurement is made 1.44 mm downstream from mix point MP. This wider channel has a surface area of $1.44\times10^{-6}$ square meters, yielding a S/V equal to $1.6\times10^4$ m$^{-1}$, which is $\frac{1}{10}^{th}$ the S/V of the narrower channel. This alone can decrease ten-fold the removal of compound per unit volume by adsorption.

This geometry change can also decrease the radial diffusive flux of compound. Flow in these small channels is at low Reynolds number, so diffusion from a point in the fluid is the only mechanism by which compound concentration changes radially in a microfluidic channel. Increasing the radius of the channel, thereby decreasing the radial diffusive flux, therefore, means that the concentration of compound at center analysis region CR of analysis region AR can be less affected by adsorption than in the smaller upstream channels.

Thus, increasing the cross-sectional area of analysis region AR of analysis channel AC can both decrease the amount of adsorption at the wall per unit volume and decrease the rate of flux of compound from center analysis region CR to any of channel walls W. Both together mean that the concentration at center analysis region CR can decrease more slowly due to adsorption of compound.

Further, in all embodiments, the surface area of all channels exposed to compounds, not just analysis channel AC, can preferably be kept minimal, especially those channels through which concentration gradients flow. This can be accomplished by making channels as short as practicable. Additionally, when the volume contained by a channel must be defined (e.g. where the channel must contain a volume of 50 nL), it is best to use larger diameters/shorter lengths wherever possible to reduce S/V.

Another benefit of increasing analysis channel AC cross-section by increasing channel diameter is that the length of the channel down which the fluid flows can be reduced. In the example given earlier, a channel with 25 µm diameter needed to be 144 mm long to enclose 90 nl whereas the channel with 250 µm diameter needed to be only 1.44 mm long. This shorter channel can be much easier to fabricate and has a much smaller footprint on a microfluidic chip.

Still another benefit of increasing analysis channel AC cross-section is that it will behave like an expansion channel, which filters noise out of chemical concentration gradients, as disclosed in co-pending, commonly assigned U.S. Provisional Application entitled MICROFLUIDIC SYSTEMS, DEVICES AND METHODS FOR REDUCING NOISE GENERATED BY MECHANICAL INSTABILITIES, U.S. Provisional Application No. 60/707,245), herein incorporated by reference in its entirety. The result is that signal to noise is larger in an analysis channel AC with larger cross-section.

Figure 17:
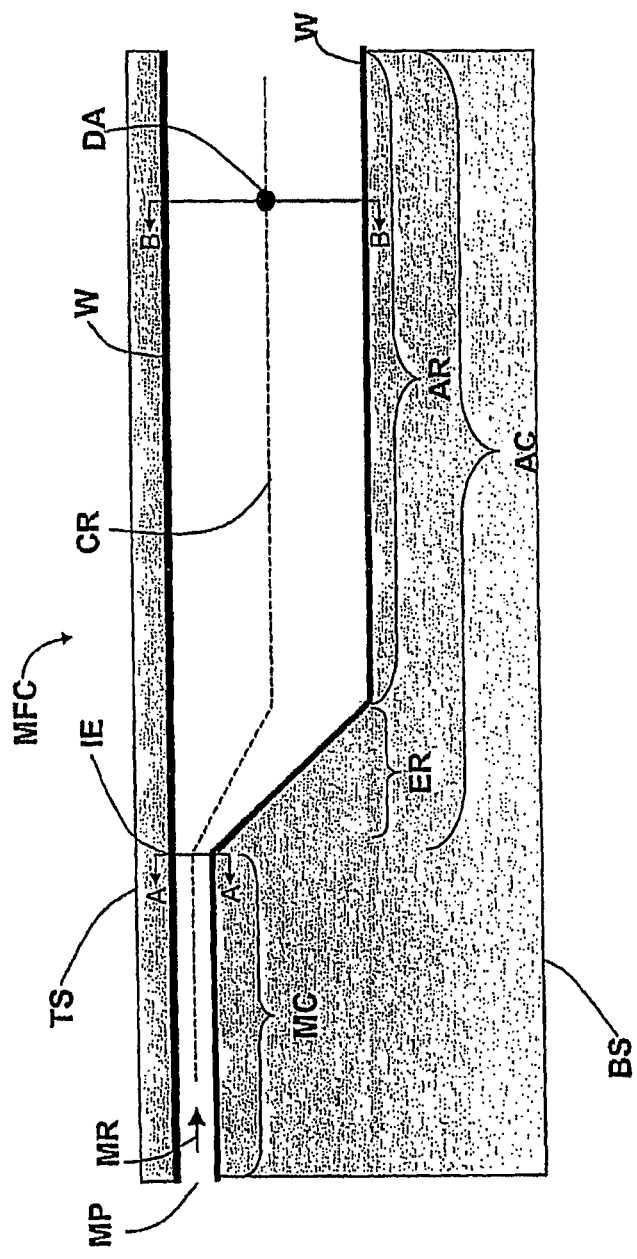
FIG. 17A is a schematic cross-sectional side view of an embodiment of analysis channel disclosed herein and, upstream fluidly communicating microscale channel.
FIG. 17B shows schematic cross-sectional cuts at A-A and B-B of the analysis channel of FIG. 17A.

FIG. 17A presents a cross-sectional side view of a portion of a microfluidic chip MFC comprising mixing channel MC and analysis channel AC depicted in FIG. 16. Microfluidic chip MFC shown in FIG. 17A can be constructed by machining channels into a bottom substrate BS and enclosing channels by bonding a top substrate TS to bottom substrate BS or otherwise forming channels within microfluidic chip MC with bottom substrate BS and top substrate TS being integral. In FIG. 17A, only the flow of merged reagent fluid stream having a flow direction indicated by arrow MR after mixing point MP is shown. Flow in a microfluidic channel can be at low Reynolds number, so the streamline of fluid that flows along center analysis region CR of the narrower mixing channel MC can travel at the mid-depth along entire mixing channel MC, becoming center analysis region CR of analysis region AR of analysis channel AC. Detection area DA can reside along center analysis region CR at a point sufficiently far downstream of mixing channel MC to permit the reaction to proceed to a desired degree.

Analysis channel AC can approximate a circular cross-section as closely as possible to produce the smallest ratio of surface area to volume, and also to produce the largest diffusion distance from centerline center analysis region CR to a channel wall W. However, microfluidic channels may not be circular in cross-section due to preferred manufacturing techniques. Rather, they can be more likely square in cross-section, with the exact shape depending on the technique used to form the channels. For such channels, a cross-section of analysis channel AC, particularly within analysis region AR, can have an aspect ratio as close to one as possible or, more precisely stated, the distance from center analysis region CR to channel wall W can be as nearly constant in all radial directions as possible.

FIG. 17B shows two different cross-sectional views along analysis channel AC as viewed along cutlines A-A and B-B. Both cross-sectional views illustrate an aspect ratio approximating one. That is, for cross-section A-A, height $H_1$ of mixing channel MC is approximately equal to width $W_1$ of mixing channel MC, such that $H_1/W_1$ approximately equals one. Comparably, for cross-section B-B, height $H_2$ of mixing channel MC is approximately equal to width $W_2$ of mixing channel MC, such that $H_2/W_2$ approximately equals one.

FIG. 17B further shows that the cross-sectional area ($H_2 \times W_2$) of analysis region AR at cutline B-B, which is located at detection area DA of analysis region AR, is significantly larger than the cross-sectional area ($H_1 \times W_1$) of input end IE at cutline A-A. In some embodiments of the presently disclosed subject matter, the cross-sectional area at detection area DA can be at least twice the value of the cross-sectional area value at input end IE and further upstream, such as in mixing channel MC. Further, in some embodiments, the cross-sectional area at detection area DA can be between about two times and about ten times the value of the cross-sectional area value at input end IE. As shown in cutline B-B of FIG. 17B, detection area DA can be positioned along center analysis region CR approximately equidistant from each of walls W to provide maximal distance from walls W, and thereby minimize effects of molecule adsorption to walls W. It is clear from FIG. 17B that the larger cross-sectional area at cutline B-B can provide both greater distance from walls W and smaller S/V than the smaller cross-sectional area at cutline A-A, both of which can reduce adsorption effects on data analysis, as discussed herein. Although detection area DA is shown in the figures as a circle having a distinct diameter, the depiction in the drawings is not intended as a limitation to the size, shape, and/or location of detection area DA within the enlarged cross-sectional area of analysis region AR. Rather, detection area DA can be as large as necessary and shaped as necessary (e.g. circular, elongated oval or rectangle, etc.) to acquire the desired data, while minimizing size as much as possible to avoid deleterious adsorption effects on the data. Determination of the optimal balance of size, shape and location while minimizing adsorption effects is within the capabilities of one of ordinary skill in the art without requiring undue experimentation.

Additional details and features of analysis channel AC are disclosed in co-pending, commonly assigned U.S. Provisional Application entitled METHODS AND APPARATUSES FOR REDUCING EFFECTS OF MOLECULE ADSORPTION WITHIN MICROFLUIDIC CHANNELS, U.S. Provisional Application No. 60/707,366, herein incorporated by reference in its entirety.

In some embodiments, the presently disclosed subject matter provides apparatuses and methods for making and using the same that can decrease the interference of adsorption to concentration dependent measurements, such as in biochemistry reactions (including $IC_{50}$ determinations), by reducing adsorption of molecules to microfluidic channel walls. In some embodiments, the presently disclosed subject matter provides microfluidic chips comprising channels and chambers with treated surfaces exhibiting reduced adsorption of molecules to channel walls, such as for example hydrophilic surfaces, and methods of preparing and using the same. In some embodiments, methods of preparing hydrophilic surfaces by treating hydrocarbon-based plastics, such as for example polycarbonate, with fluorine gas mixtures are provided. In some exemplary embodiments, the methods comprise contacting a mixture of fluorine gas and an inert gas with the surface to be treated, then flushing the surface with air. This treatment results in plastic surfaces of increased hydrophilicity (increased surface energy). Hydrophobic solutes, in particular known and potential drug compounds, in solutions in contact with these treated hydrophilic plastic surfaces are less likely to be adsorbed onto the more hydrophilic surfaces. Plastics comprising the treated surfaces are useful in providing many improved drug discovery and biochemical research devices for handling, storing, and testing solutions containing low concentrations of hydrophobic solutes.

Additional details and features of hydrophilic surfaces in microfluidic systems and methods of making and using the same are disclosed in co-pending, commonly owned U.S. Provisional Application entitled PLASTIC SURFACES AND APPARATUSES FOR REDUCED ADSORPTION OF SOLUTES AND METHODS OF PREPARING THE SAME, U.S. Provisional Application No. 60/707,288.

Further, in some embodiments of the presently disclosed subject matter, microfluidic systems are provided comprising an analysis channel with an enlarged cross-sectional area and a reduced surface area to volume ratio and further comprising channels and chambers with hydrophilic surfaces.

It will be understood that various details of the invention may be changed without departing from the scope of the invention. Furthermore, the foregoing description is for the purpose of illustration only, and not for the purpose of limitation.

What is claimed is:

1. A pump for producing low, non-pulsatile liquid flow rates, comprising:
   (a) a motor drive having a gear reduction for producing liquid flow rates grading from substantially between 0 nl/min and 500 nl/min, with a precision as low as approximately 0.1 nl/min;
   (b) a lead screw coupled to the motor drive for rotatable actuation thereby and having a thread pitch for producing liquid flow rates grading from substantially between 0 nl/min and 500 nl/min, with a precision as low as approximately 0.1 nl/min;
   (c) a stage engaging the lead screw and linearly translatable thereby;
   (d) a barrel for containing a liquid and having an internal volume ranging from approximately 5 to approximately 500 μl;
   (e) a plunger extending into the barrel and coupled to the stage for translation therewith;
   (f) a microfluidic interconnect device for removably coupling a fluid conduit with the barrel, wherein the fluid conduit places the barrel in fluid communication with a microfluidic chip;
   (g) a PUMP housing enclosing the motor drive, the lead screw, the stage, the barrel, the plunger, and the interconnect device; and
   (h) a temperature regulating device also mounted in the PUMP housing for regulating a temperature of the microfluidic chip, which is enclosed within said temperature regulating device.

2. The pump according to claim 1 wherein the motor drive comprises a motor drive selected from the group consisting of a servo motor drive and a stepper motor drive.

3. The pump according to claim 1 wherein the gear reduction is approximately 1024:1.

4. The pump according to claim 1 wherein the thread pitch is approximately 80 threads per inch.

5. The pump according to claim 1 further comprising a fastener removably securing the motor drive to the housing, wherein the motor drive is axially adjustable relative to the barrel for accommodating different lengths of plungers or barrels.

6. The pump according to claim 1 further comprising a fastener removably securing the motor drive to the housing, wherein the motor drive is axially adjustable relative to the barrel for accommodating syringes at different positions.

7. The pump according to claim 1 wherein the PUMP housing is thermally insulated.

8. The pump according to claim 1 further comprising a coupling device interconnecting the plunger and the stage.

9. The pump according to claim 8 wherein the coupling device comprises a plunger clasp attached to the stage and a tightening plate adjustably secured to the stage by a fastener, wherein a head portion of the plunger is securable between the plunger clasp and the tightening plate.

10. The pump according to claim 8 comprising a wherein the pump housing encloses the coupling device.

11. The pump according to claim 1 wherein the interconnect device comprises a first fitting removably attached to the barrel and a second fitting removably attached to the first fitting for fluidly coupling the fluid conduit with the barrel.

* * * * *